United States Patent
Tanaka et al.

[11] Patent Number: 5,321,135
[45] Date of Patent: Jun. 14, 1994

[54] PROCESS FOR THE PREPARATION OF POLYCYCLIC COMPOUNDS USING FERRIC PERCHLORATE AND ACID TRIFLUOROACIDIC

[75] Inventors: Masahide Tanaka; Takeshi Wakamatsu, both of Ami; Hiroshi Mitsuhashi, deceased, late of Ichihara; by Mieko Mitsuhashi, heiress, Tokyo; by Hiroyuki Mitsuhashi, heir, Hokkaido; by Tomoai Mitsuhashi, heir, Tokyo, all of Japan

[73] Assignee: Tsumura & Co., Tokyo, Japan

[21] Appl. No.: 876,581

[22] Filed: Apr. 30, 1992

[30] Foreign Application Priority Data

Apr. 30, 1991 [JP] Japan ................................. 3-124484

[51] Int. Cl.$^5$ ................. C07D 307/93; C07D 317/54; C07D 407/08; C07D 407/10
[52] U.S. Cl. .................................. 540/455; 540/454; 540/468; 540/476; 549/383
[58] Field of Search ............... 540/468, 476, 454, 455; 549/383

[56] References Cited

FOREIGN PATENT DOCUMENTS

WO87/05286 9/1987 PCT Int'l Appl. ................ 540/465

OTHER PUBLICATIONS

Cambie et al., Chemical Abstracts, vol. 94, #174760d (1981).
Landais et al., Tetrahedron Letters, vol. 27, No. 16, pp. 1785–1788 (1986).
Landais et al. II, Tetrahedron Letters, vol. 27, No. 44, pp. 5377–5380 (1986).
Landais et al. III, Tetrahedron Letters, vol. 28, No. 43, pp. 5161–5164 (1987).
Landais et al. IV, Tetrahedron, vol. 47, No. 23, pp. 3787–3804 (1991).
Robin et al. I, Chemical Abstracts, vol. 110, #75090c (1989).
Robin et al. II, J. Org. Chem., vol. 53, pp. 224 to 226 (1988).
Ronlan et al., J. Org. Chem., vol. 39, pp. 1014 to 1016 (1974).
Chemical Abstracts, vol. 115, No. 16, Oct. 21, 1991, No. 168941Az, J. B. Fernandez, et al., "Synthesis of Dibenzocyclooctadiens by Anodic Oxidation".

Primary Examiner—Floyd D. Higel
Attorney, Agent, or Firm—Oblon, Spivak, McClelland, Maier & Neustadt

[57] ABSTRACT

Polycyclic compounds (I) can be prepared in accordance with the following reaction formula:

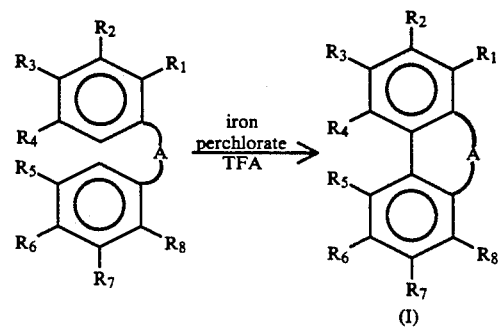

wherein $R_1$–$R_8$ each represents a hydrogen atom, a hydroxyl group, an alkoxyl group or a substituted or unsubstituted benzyloxy group or neighboring two groups of $R_1$–$R_8$ are coupled together to form an alkylenedioxy group; and A is an alkylene group which may be substituted by one or more alkoxycarbonyl groups, an alkenylene group which may be substituted by one or more alkoxycarbonyl groups, or a group represented by any one of the following formulas:

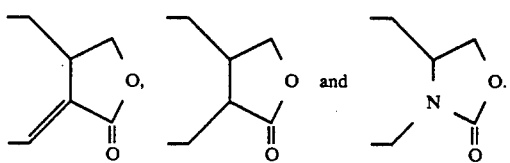

1 Claim, No Drawings

PROCESS FOR THE PREPARATION OF POLYCYCLIC COMPOUNDS USING FERRIC PERCHLORATE AND ACID TRIFLUOROACIDIC

BACKGROUND OF THE INVENTION

1) Field of the Invention

The present invention relates to a process for preparing polycyclic compounds.

2) Description of the Related Art

Owing to recent developments in instrumental analyses and compound-isolating means, effective ingredients in crude drugs have been isolated and identified. Chemical syntheses of effective ingredients in crude drugs have been tried based on the above results. Crude drugs, however, include many compounds whose chemical syntheses are extremely difficult because of the presence of a complex ring system. Such difficulties still remain as an obstacle for the establishment of chemical processes for the synthesis of such crude drug ingredients in more than a few instances.

For example, some compounds containing a dibenzocyclooctane or benzocyclooctene ring represented by the following formula:

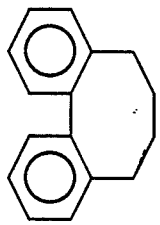

have been known as effective ingredients of crude drugs. It is, however, difficult to synthesize the above ring system in any manner known to date. It has therefore been regarded difficult to industrially prepare these ingredients by a chemical synthesis process.

Determination of an effective ingredient of a crude drug makes it possible to administer only the effective ingredient in order to prevent side effects and reduce the dosage of the crude drug. This is certainly considered preferable. Extraction of only an effective ingredient from a crude drug is accompanied with the drawbacks that an extra complicated step is required to remove other ingredients and the yield is poor. Further, the amount of production of the crude drug source itself is limited, resulting in problems in both economy and resource.

SUMMARY OF THE INVENTION

There is, hence, an outstanding demand for the development of an industrially acceptable process for the synthesis of polycyclic compounds.

The present inventors have conducted an extensive research on coupling reactions for the synthesis of polycyclic compounds. As a result, it has been found that a polycyclic compound represented by the following formula (I):

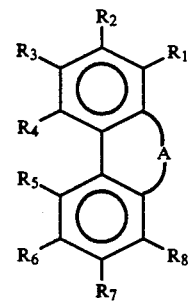

wherein $R_1$–$R_8$ each represents a hydrogen atom, a hydroxyl group, an alkoxyl group or a substituted or unsubstituted benzyloxy group or neighboring two groups of $R_1$–$R_8$ are coupled together to form an alkylenedioxy group; and A is an alkylene group which may be substituted by one or more alkoxycarbonyl groups, an alkenylene group which may be substituted by one or more alkoxycarbonyl groups, or a group represented by any one of the following formulas:

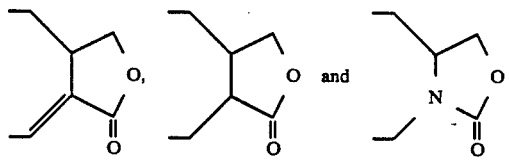

can be prepared by reacting a compound, represented by the following formula (II):

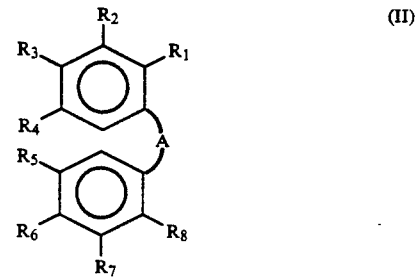

wherein $R_1$–$R_8$ and A have the same meanings as defined above, with an iron perchlorate in the presence of trifluoroacetic acid, leading to the completion of the invention.

Namely, the present invention provides a process for preparing a polycyclic compound represented by the formula (I), which comprises reacting a compound represented by the formula (II) with trifluoroacetic acid in the presence of an iron perchlorate.

According to the process of the present invention, polycyclic compounds which have heretofore been available only from natural resources can each be prepared easily from a compound having two benzene rings in a molecule. The process is, therefore, extremely useful as a process for the preparation of drugs or intermediates for chemical syntheses.

DETAILED DESCRIPTION OF THE INVENTION AND PREFERRED EMBODIMENTS

To practice the process of this invention, it is only necessary to use iron perchlorate in an amount of at least 2 moles, preferably about 2-3 moles, and trifluoroacetic acid in an amount of at least 5 moles, preferably about 5-100 moles, both per mole of the compound (II), and then to react them at about −10° C. to 30° C. for about 0.5-3 hours in an organic solvent such as a halogenated hydrocarbon, e.g., methylene chloride or chloroform, or an aromatic hydrocarbon, e.g., toluene or benzene. In this manner, the compound represented by the formula (I) can be prepared.

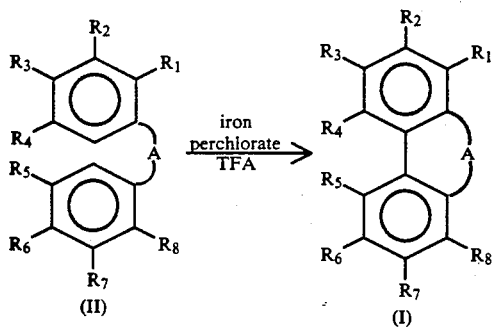

Examples of the compound (II), which is the starting material in the present invention, include compounds represented by the formula (II'). Compounds (II') include certain novel compounds. They can each be prepared by the reaction of a benzaldehyde derivative (IV) and a compound (III) according to the following reaction formula. The compound (III) is either a known compound or can be easily synthesized following a process for the preparation of a known compound.

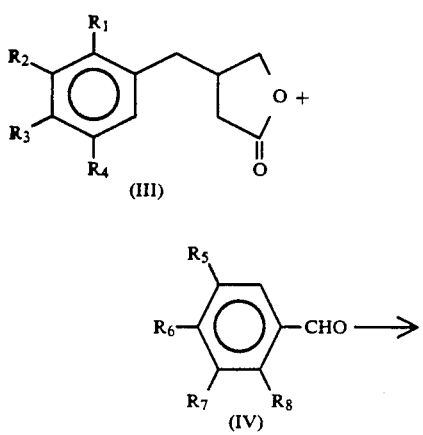

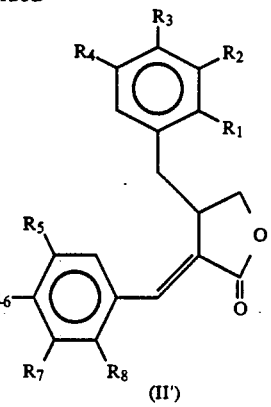

wherein $R_1$-$R_8$ have the same meanings as defined above.

Examples of the iron perchlorate, said examples being usable in the present invention, include ferric perchlorate.

The optical activity of the starting compound (II), if any, is retained in the above reaction so that the compound (I) of the present invention can be obtained in an optically active form by using an optically active compound (II).

The compound (I) of the present invention obtained as described above can be readily converted to a desired compound by subjecting it to partial ring opening, reduction, oxidation, side-chain cutting, chemical modification or the like, as needed.

The present invention will next be described in detail by the following referential examples and examples.

EXAMPLE 1

Preparation of (3aRS,SRbiar)-3a,4-dihydro-6,7,8,9,10,11-hexamethoxydibenzo[4,5:6,7]-cycloocta[1,2-c]furan-1(3H)-one (1) First process using ferric perchlorate Ferric perchlorate (9.37 g, 20.3 mmol) was added to a solution of (RS)-(E)-2-(3,4,5-trimethoxybenzylidene)-3-[1-(3,4,5-trimethoxyphenyl)methyl]-butanolide [3.0 g, 6.8 mmol, Y. Landais, Alebrun, and J. P. Robin, Tetrahedron Lett., 27, 5377, (1986)] in trifluoroacetic acid (20 ml), followed by stirring at room temperature for 2.5 hours. Trifluoroacetic acid was distilled off under reduced pressure. The residue was diluted with 60 ml of ethyl acetate. The resulting solution was washed with water, a saturated aqueous solution of sodium bicarbonate (hereinafter called "saturated NaHCO₃"), water and a saturated aqueous solution of sodium chloride (hereinafter called "saturated NaCl"). The organic layer was then dried over anhydrous magnesium sulfate. The solvent was distilled off under reduced pressure, whereby 3.1 g of colorless oil were obtained. The oil was purified by column chromatography (silica gel: "MERCK #9385", 30 g, eluent: 1:1 mixed solvent of ether and benzene), whereby 2.66 g of the title compound were obtained as a colorless solid (yield: 89%).

(2) Second process using ferric perchlorate

A solution of (RS)-(E)-2-(3,4,5-trimethoxybenzylidene)-3-[1-(3,4,5-trimethoxyphenyl)methyl]-butanolide (100 mg, 0.23 mmol) in methylene chloride (1 ml) was added with 0.1 ml of trifluoroacetic acid and further with ferric perchlorate (0.30 g, 0.65 mmol), followed by stirring at room temperature for 1 hour. The reaction mixture was dissolved in 10 ml of ethyl acetate. The resulting solution was washed with 10 ml of 2N-HCl and then with 10 ml of saturated NaCl. The organic layer was then dried over anhydrous magnesium sulfate. The solvent was distilled off under reduced pressure, whereby 107 mg of brown oil were obtained. The oil was purified by column chromatography (silica gel: "MERCK #9385", 5 g, eluent: 1:1 mixed solvent of ethyl acetate and hexane), whereby 81 mg of the title compound were obtained as pale yellow oil (yield: 81%). Melting point: 153.5°-154.5° C. (Colorless prism crystals recrystallized from ethyl acetate-hexane)

$^1$HNMR (CDCl$_3$): 2.45(1H,d,J=14Hz), 3.06(1H,dd,J=7,14Hz), 3.44-3.64(1H,m), 3.59(3H,s), 3.64(3H,s), 3.88(3H,s), 3.89(3H,s), 3.90(3H,s), 3.91(3H,s), 4.11(1H,dd,J=9,10Hz), 4.47(1H,t,J=9Hz), 6.41(1H,s), 6.59(1H,s), 7.53(1H,d,J=3Hz).

IR $\gamma$max (KBr) cm$^{-1}$: 2936, 2836, 1758, 1674, 1594, 1488, 1462, 1406, 1346, 1318, 1238, 1200, 1060, 1016, 928.

MS: 442 (M+, base)

REFERENTIAL EXAMPLE 1

Synthesis of
2,3-bis[1-(3,4,5-trimethoxyphenyl)-methyl]butanolide

Triethylsilane (6 ml, 37.8 mmol) and the Wilkinson's complex (5 mg, 0.0054 mmol) were added to a solution of (RS)-(E)-2-(3,4,5-trimethoxybenzylidene)-3-[1-(3,4,5-trimethoxyphenyl)methyl]butanolide (324.3 mg, 0.73 mmol) in toluene (6 ml), followed by stirring at 110° C. for 30 minutes. The solvent was distilled off under reduced pressure and the residue was dissolved in 2 ml of dichloromethane. The resulting solution was added with 0.5 ml of 2N-HCl, followed by stirring at room temperature for one hour. The reaction mixture was thereafter dissolved in 20 ml of ethyl acetate. The resulting mixture was washed with water and then with saturated NaHCO$_3$. The organic layer was then dried over anhydrous magnesium sulfate. The solvent was distilled off under reduced pressure, whereby 470 mg of brown oil were obtained. The oil was purified by column chromatography (silica gel: "MERCK #9385", 15 g, eluent: 1:4 mixed solvent of ethyl acetate and hexane), whereby 270 mg of the title compound were obtained as colorless oil (yield: 83%).

$^1$NMR (CDCl$_3$): 2.44-2.71(4H,m), 2.97(2H,d,J=5Hz), 3.80(6H,s), 3.81(6H,s), 3.82(6H,s), 4.08-4.27(2H,m), 6.21(1.6H,s), 6.28(0.4H,s), 6.38(1.6H,s), 6.53(0.4H,s).

MS: 446 (M+), 181 (base).

EXAMPLE 2

Synthesis of 3a,4,13,13a-tetrahydro-6,7,8,9,10,11-hexamethoxydibenzo[4,5:6,7]cycloocta[1,2-c]furan-1(3H)-one Dissolved in a mixture consisting of 0.5 ml of dichloromethane and 0.05 ml of trifluoroacetic acid were 50 mg (0.112 mmol) of 2,3-bis[1-(3,4,5-trimethoxyphenyl)-methyl]butanolide. The solution was added with 150 mg (0.32 mmol) of ferric perchlorate, followed by stirring at room temperature for 19 hours. The reaction mixture was dissolved in 10 ml of ethyl acetate. The resulting solution was washed successively with 2N-HCl, water and saturated NaHCO$_3$. The organic layer was then dried over anhydrous magnesium sulfate. The solvent was distilled off under reduced pressure, whereby colorless oil was obtained. The oil was purified by thinlayer chromatography (TLC) (silica gel: "MERCK #5744", eluent: 1:3 mixed solvent of acetone and hexane), whereby 28.5 mg of the title compound were obtained as a colorless solid (yield: 57%).

$^1$NMR (CDCl$_3$): 2.10-2.72(5H,m), 3.16(1H,d,J=13Hz), 3.60(2.4H,s), 3.62(2.4H,s), 3.65(0.6H,s), 3.66(0.6H,s), 3.67-3.90(1H,m), 3.87(6H,s), 3.90(3H,s), 3.91(3H,s), 4.34-4.48(1H,m), 6.38(0.2H,s), 6.53(0.8H,s), 6.64(0.8H,s), 6.74(0.2H,s).

IR $\gamma$max (KBr) cm$^{-1}$: 2936, 1778, 1596, 1492, 1462, 1454, 1402, 1328, 1200, 1126, 1104, 990.

MS: 444 (M+, base)

REFERENTIAL EXAMPLE 2

Synthesis
(RS)-(E)-3-[1-(5-methoxy-3,4-methylenedioxyphenyl)-methyl]-2-(3,4,5- trimethoxybenzylidene)butanolide Sodium hydride (60%, 0.43 g, 10.8 mmol) and methanol (0.016 ml, 0.4 mmol) were added to 20 ml of toluene under an argon stream. The solution was added further with (RS)-3-[1-(5-methoxy-3,4-methylenedioxyphenyl)-methyl]butanolide [1.0 g, 4 mmol, G. E. Schneiders and R. Stevenson, J. Chem. Soc. Perkin I, 999, (1982)] and 3,4,5-trimethoxybenzaldehyde (1.24 g, 6.3 mol), followed by stirring at room temperature for 24 hours. The reaction mixture was added with 2N-HCl. The solution was dissolved in ethyl acetate, from which the water layer was removed. The organic layer was washed with saturated NaCl and then, dried over anhydrous magnesium sulfate. The solvent was distilled off. The residue thus obtained was purified by column chromatography (silica gel: "MERCK #9385", 50 g, eluent: 1:2 mixed solvent of ethyl acetate and hexane), whereby 732 mg of the title compound were obtained as a colorless solid (yield: 43%).

Melting point: 132°-132.5° C. (Colorless prism crystals recrystallized from ethyl acetate-hexane)

$^1$HNMR (CDCl$_3$): 2.64(1H,dd,J=10,14Hz), 3.02(1H,dd,J=5,14Hz), 3.66-3.90(1H,m), 3.87(3H,s), 3.89(6H,s), 3.91(3H,s), 4.24-4.31(2H,m), 5.94(2H,s), 6.29(1H,d,J=1Hz), 6.34(1H,d,J=1Hz), 6.77(2H,s), 7.52(1H,d,J=2Hz).

IR $\gamma$max (KBr) cm$^{-1}$: 2940, 1748, 1644, 1582.
MS: 428 (M+), 165 (base).
Elemental analysis (as $C_{23}H_{24}O_8$): Calculated: C, 64.48; H, 5.65; Found: C, 64.48; H, 5.67.

EXAMPLE 3

Synthesis of
(3aRS,SRbiar)-3a,4-dihydro-8,9,10,11-tetramethoxy-6,7-methylenedioxydibenzo[4,5:6,7]cycloocta[1,2-c]furan-1(3H)-one and
(3aRS,SRbiar)-3a,4-dihydro-6,9,10,11-tetramethoxy-7,8-methylenedioxydibenzo[4,5:6,7]cycloocta[1,2-c]furan-1(3H)-one Ferric perchlorate hexahydrate (150 mg, 0.324 mmol) and trifluoroacetic acid (0.05 ml) were added at room temperature to a solution of (RS)-(E)-3-[1-(5-methoxy-3,4-methylenedioxyphenyl)methyl]-2-(3,4,5-trimethoxybenzylidene)butanolide (50 mg, 0.117 mmol) in dichloromethane (0.5 ml), followed by stirring at the same temperature for 3.5 hours. The reaction mixture was washed successively with 2N-HCl, water and saturated NaHCO$_3$. The organic layer was then dried over anhydrous magnesium sulfate. The solvent was distilled off under reduced pressure. The brown oil thus obtained (52 mg) was purified by TLC (silica gel: "MERCK #5744", eluent: 1:1 mixed solvent of benzene and ether), whereby 23 mg of colorless oil were obtained from fractions containing (3aRS,SRbiar)-3a,4-dihydro-8,9,10,11-tetramethoxy-6,7-methylenedioxydibenzo-[4,5:6,7]cycloocta[1,2-c]furan-1(3H)-one (yield: 46%) and 3.7 mg of colorless oil were obtained from other fractions containing (3aRS, SRbiar)-3a,4-dihydro-6,9,10,11-tetramethoxy-7,8-methylenedioxydibenzo-[4,5:6,7]cycloocta[1,2-c]furan-1(3H)-one (yield: 7%), respectively. *(3aRS,SRbiar)-3a,4-dihydro-8,9,10,11-tetramethoxy-6,7-methylenedioxydibenzo[4,5:6,7]cycloocta[1,2-c]furan-1(3H)-one:

$^1$HNMR (CDCl$_3$): 2.42(1H,dd,J=1.5,14Hz), 3.00(1H,dd,J=7,14Hz), 3.42–3.60(1H,m), 3.63(3H,s), 3.81(3H,s), 3.89(3H,s), 3.91(3H,s), 4.44(1H,t,J=9Hz), 4.09(1H,dd,J=9,10Hz), 5.96(1H,d,J=1.5Hz), 5.98(1H,d,J=1.5Hz), 6.58(1H,s), 6.34(3H,s), 7.51(1H,d,J=2Hz).

IR $\gamma$max (CHCl$_3$) cm$^{-1}$: 2964, 2940, 1754, 1674, 1620, 1590. MS: 426 (M$^+$, base). *(3aRS,SRbiar)-3a,4-dihydro-6,9,10,11-tetramethoxy-7,8-methylenedioxydibenzo[4,5:6,7]cycloocta[1,2-c]furan-1(3H)-one:

$^1$HNMR (CDCl$_3$): 2.45(1H,dd,J=1,14Hz), 3.07(1H,dd,J=7,14Hz), 3.43–3.64(1H,m), 3.72(3H,s), 3.89(3H,s), 3.91(3H,s), 3.94(3H,s), 4.12(1H,dd,J=8,10Hz), 4.47(1H,t,J=9Hz), 5.88(1H,d,J=1Hz), 5.98(1H,d,J=1Hz), 6.28(1H,s), 6.62(1H,s), 7.51(1H,d,J=2.5Hz).

IR $\gamma$max (CHCl$_3$) cm$^{-1}$: 2936, 1754, 1674, 1644, 1592. MS: 426 (M$^+$, base).

REFERENTIAL EXAMPLE 3

Synthesis of (RS)-(E)-3-[1-(3,4-dihydroxy-5-methoxyphenyl)methyl]-2-(3,4,5-trimethoxybenzylidene)-butanolide:

A dichloromethane solution (1.0M, 4.7 ml, 4.7 mmol) of boron trichloride was added at 0° C. to a solution of (RS)-(E)-3-[1-(5-methoxy-3,4-methylenedioxyphenyl)-methyl]-2-(3,4,5-trimethoxybenzylidene)butanolide (1.0 g, 2.34 mmol) in dichloromethane (5 ml), followed by stirring at the same temperature for 40 minutes. The solvent was distilled off under reduced pressure. The residue was added with 15 ml of methanol and 4N-HCl, followed by stirring at room temperature for 45 minutes. The reaction mixture was dissolved in 20 ml of ethyl acetate. The resulting mixture was washed with water and then with saturated NaCl. The organic layer was then dried over anhydrous magnesium sulfate. The solvent was distilled off under reduced pressure, whereby 747 mg of the title compound were obtained as yellow foam (yield: 77%).

1HNMR (CDCl$_3$): 2.61(1H,dd,J=10,14Hz), 3.04(1H,dd,J=5,14Hz), 3.83(3H,s), 3.89(6H,s), 3.90(3H,s), 3.83–3.97(1H,m), 4.25–4.30(2H,m), 5.34(1H,s), 5.30(1H,s), 6.44(1H,d,J=2Hz), 6.23(1H,d,J=2Hz), 6.79(2H,s), 7.52(1H,d,J=2Hz).

EXAMPLE 4

Synthesis of (3aRS,SRbiar)-3a,4-dihydro-6,7-dihydroxy-8,9,10,11-tetramethoxydibenzo[4,5:6,7]-cycloocta[1,2-c]furan-1(3H)-one Dissolved in a mixture of 25 ml of dichloromethane and 25 ml of trifluoroacetic acid were 828 mg (2.0 mmol) of (RS)-(E)-3-[1-(3,4-dihydroxy-5-methoxyphenyl)methyl]-2-(3,4,5-trimethoxybenzylidene)-butanolide. The solution was added with 1.93 g (4.17 mmol) of ferric perchlorate, followed by stirring at room temperature for one hour. The reaction mixture was added with saturated NaHSO$_3$ and further with 50 ml of ethyl acetate. The organic layer was washed with saturated NaHCO$_3$ and then with saturated NaCl, followed by drying over anhydrous magnesium sulfate. The solvent was distilled off under reduced pressure, whereby 740 mg of a brown solid were obtained. The solid was washed with ether and the remaining crystals were collected by filtration, whereby 573 mg of the title compound were obtained as pale-brown prism crystals (yield: 70%).

Melting point: 246°–246.5° C. (methanol)

IR $\gamma$max (KBr) cm$^{-1}$: 3548, 3364, 2940, 1740, 1670, 1620, 1590, 1492, 1200.

MS 414 (M$^+$, base).

1HNMR: 2.42(1H,dd,J=1.5,14Hz), 3.02(1H,dd,J=7,14Hz), 3.40–3.60(1H,m), 3.31(3H,s), 3.57(3H,s), 3.91(3H,s), 3.93(3H,s), 4.11(1H,dd,J=8,10Hz), 4.46(1H,t,J=9Hz), 5.38(1H,s), 5.54(1H,s), 6.62(1H,s), 6.51(1H,s), 7.50(1H,d,J=3.4Hz).

REFERENTIAL EXAMPLE 4

Synthesis of (R)-(E)-2-(3,4,5-trimethoxybenzylidene)-3-[1-(3,4,5-trimethoxyphenyl)-methyl]butanolide:

A solution of (R)-3-[1-(3,4,5-trimethoxyphenyl)-methyl]butanolide [10.52 g, 0.04 mol; K. Lalami, D. Dhai, and E. Brown, Heterocycles, 27, 1131 (1988)] and 3,4,5-trimethoxybenzaldehyde (11.4 g, 0.058 mol) in toluene (150 ml) was cooled to 0° C. under an argon stream. The solution was added with 4.0 g of sodium hydride (60%, 0.1 mol) and 0.15 ml (0.0037 mol) of methanol, followed by stirring at room temperature for 45 hours. The reaction mixture was ice-cooled and then added with 100 ml of 2N-HCl. After the removal of the water layer, the organic layer was washed successively with water, saturated NaHCO$_3$ and saturated NaCl and then dried over anhydrous magnesium sulfate. The solvent was distilled off. The residue thus obtained (20 g) was purified by column chromatography on a silica gel column (silica gel: "MERCK #9385", 500 g, eluent: 1:2 mixed solvent of ethyl acetate and hexane), whereby 5.71 g of the title compound were obtained as pale yellow oil (yield: 33%). [$\alpha$]$^{27}$$_D$: $-75.64°$ (C=0.55, CHCl$_3$)

$^1$HNMR (CDCl$_3$): 2.64(1H,dd,J=10,14Hz), 3.10(1H,dd,J=4,14Hz), 3.81–3.96(1H,m), 3.81(3H,s), 3.83(6H,s), 3.89(6H,s), 3.91(3H,s), 4.29–4.32(1H,m), 6.82(2H,s), 6.38(2H,s), 7.53(1H,d,J=1.5Hz).

IR $\gamma$max (CHCl$_3$) cm$^{-1}$: 2940, 2840, 1746, 1648, 1586.

MS: 444 (M$^+$), 181 (base).

HRMS (as C$_{24}$H$_{28}$O$_8$, M$^+$): Calculated: 444.17844; Found: 444.17894.

EXAMPLE 5

Synthesis of (3aR,Sbiar)-3a,4-dihydro-6,7,8,9,10,11-hexamethoxydibenzo[4,5:6,7]-cycloocta[1,2-c]furan-1(3H)-one A solution of (R)-(E)-2-(3,4,5-trimethoxybenzylidene)-3-[1-(3,4,5-trimethoxyphenyl)methyl]-butanolide (5.6 g, 0.013 mol) in methylene chloride (50 ml) was added with 5 ml of trifluoroacetic acid and further with 16.8 g (0.036 mmol) of ferric perchlorate, followed by stirring at room temperature for 2 hours. The reaction mixture was washed successively with 50 ml of water and 50 ml of 2N-HCl. The organic layer was then dried over anhydrous magnesium sulfate. The solvent was distilled off under reduced pressure, whereby 6.9 g of brown oil were obtained. The oil thus obtained was purified by column chromatography (silica gel: "MERCK #9385", 50 g, eluent: 1:1 mixed solvent of ethyl acetate and hexane), whereby 5.18 g of the title compound were obtained as pale yellow oil (yield: 93%).

$^1$HNMR (CDCl$_3$): 2.46(1H,dd,J=1,14Hz), 3.06(1H,dd,J=6,6,14Hz), 3.43–3.59(1H,m), 3.59(3H,s), 3.64(3H,s), 3.88(3H,s), 3.89(3H,s), 3.90(3H,s), 3.91(3H,s), 4.10(1H,dd,J=8.5,10Hz), 4.47(1H,t,J=9Hz), 6.59(1H,s), 6.41(1H,s), 7.53(1H,d,J=3Hz).

IR $\gamma$max (CHCl$_3$) cm$^{-1}$: 2940, 2840, 1756, 1674, 1596, 1484, 1460, 1398, 1346, 1316.

MS: 442 (M$^+$, base)

HRMS (as C$_{24}$H$_{26}$O$_8$; M$^+$): Calculated: 442.16279; Found: 442.16279.

REFERENTIAL EXAMPLE 5

Synthesis of 1-methyl hydrogen (R)-2-[1-(5-methoxy-3,4-methylenedioxyphenyl)methyl]butanedioate Dissolved in 120 ml of hot acetone were 10 g of 1-methyl hydrogen (RS)-2-[1-(5-methoxy-3,4-methylenedioxyphenyl)methyl]butanedioate [racemic mixture, G. E. Schneider and R. Stevenson, J. Chem. Soc. Perkin 1, 999(1982)] and 4.33 g of L-(−)-α-aminocaprolactam, followed by stirring at room temperature for 3 hours. The precipitated crystals were collected by filtration, whereby 10.72 g of the aminocaprolactam salt of the title compound were obtained. The salt was dissolved in 100 ml of saturated NaHCO$_3$. After washed with ether (100 ml×3), the solution was made acidic with a 10% aqueous oxalic acid solution, followed by extraction with dichloromethane (200 ml×3). The dichloromethane extracts were combined, washed with saturated NaCl and then dried over anhydrous magnesium sulfate. The solvent was distilled off under reduced pressure, whereby 6.69 g of the title compound of 40% e.e. were obtained. After the compound was stirred in 7 ml of methanol at room temperature for 1 hour, insoluble matter was removed by filtration. The filtrate was distilled off under reduced pressure, whereby 2.05 g of the title compound of 100% e.e. were obtained.

Melting point: 97.5°–98° C. (Colorless needle crystals recrystallized from methanol)

1HNMR: 2.46(1H,dd,J=5,17Hz), 2.62–2.77(2H, m), 2.93–3.13(2H,m), 3.69(3H,s), 3.88(3H,s), 5.94(2H,s), 6.31(1H,s), 6.34(1H,s).

$[\alpha]^{23}_D$: +27.4 (C=0.985, CHCl$_3$)

IR $\gamma$max (KBr) cm$^{-1}$: 3148, 2912, 1726, 1678, 1638, 1510.

MS: 296 (M$^+$), 165 (base).

Elemental analysis (as C$_{14}$H$_{16}$O$_7$): Calculated: C, 56.75; H, 5.44; Found: C, 56.69; H, 5.37.

REFERENTIAL EXAMPLE 6

Synthesis of (R)-3-[1-(5-methoxy-3,4-methylenedioxyphenyl)methyl]butanolide

Dissolved in 400 ml of ethanol were 32.0 g (0.108 mol) of 1-methyl hydrogen (R)-2-[1-(5-methoxy-3,4-methylenedioxyphenyl)methyl]butanedioate, followed by the addition of a solution of potassium hydroxide (85%, 7.44 g, 0.113 mol) in ethanol (200 ml). Under ice cooling, the solution was added with 23.0 g (0.21 mol) of calcium chloride and 16 g (0.42 mol) of sodium borohydride, followed by stirring at 0° C. for 17 hours. Under ice cooling, the reaction mixture was added with 500 ml of 6N-HCl. After stirred at room temperature for additional 1.5 hours, the resulting solution was extracted with methylene chloride (200 ml ×3). The organic layers were combined, washed with saturated NaCl, and then dried over anhydrous magnesium sulfate. The solvent was distilled off under reduced pressure, whereby 27.23 g of a colorless solid were obtained. The solid thus obtained was recrystallized from a mixed solvent of ethyl acetate and hexane, whereby 22.57 g of the title compound were obtained as colorless prism crystals (yield:83.5%).

Melting point: 88°–89° C.

$[\alpha]^{23}_D$: +7.12° (C=1.095, CHCl$_3$)

1HNMR (CDCl$_3$): 2.45(1H,dd,J=6,7Hz), 2.55–2.70(3H,m), 2.74–2.88(1H,m), 3.90(3H,s), 4.03(1H,dd,J=5.5,9Hz), 4.34(1H,dd,J=6.7,9Hz), 5.95(2H,s), 6.30(1H,d,J=1.5Hz), 6.34(1H,d,J=1.5Hz).

IR $\gamma$max (KBr) cm$^{-1}$: 1782, 1632, 1508.

MS: 250 (M$^+$), 165 (base).

Elemental analysis (as C$_{13}$H$_{14}$O$_5$): Calculated: C, 62.39; H, 5.64; Found: C, 62.36; H, 5.76.

REFERENTIAL EXAMPLE 7

Synthesis of (R)-(E)-3-[1-(5-methoxy-3,4-methylenedioxyphenyl)methyl]-2-(3,4,5-trimethoxybenzylidene)butanolide A solution of (R)-3-[1-(5-methoxy-3,4-methylenedioxyphenyl)methyl]butanolide (21.0 g, 0.084 mol) and 3,4,5-trimethoxybenzaldehyde (26.0 g, 0.133 mol) in toluene (350 ml) was cooled to 0° C. under an argon stream, followed by the addition of sodium hydride (60%, 9.1 g, 0.228 mol) and methanol (0.33 ml, 0.0082 mol). After stirred at 0° C. for 15 minutes and then at room temperature for 18 hours, the reaction mixture was ice cooled and then acidified with 2N-HCl. After the addition of ethyl acetate (100 ml), the organic layer was separated. The water layer was extracted with ethyl acetate (50 ml×2). The extracts were combined with the previously-obtained organic layer. The organic layer was washed successively with water, saturated NaHCO$_3$ and saturated NaCl, followed by drying over anhydrous magnesium sulfate. The solvent was distilled off. The residue thus obtained (52.9 g) was purified by column chromatography (silica gel: "MERCK #9385", 500 g, eluent: 1:2 mixed solvent of ethyl acetate and hexane), whereby 16.62 g of the title compound were obtained as colorless oil (yield: 46%).

$[\alpha]^{27}_D$: −53.7° (C=1.04, CHCl$_3$)

$^1$HNMR (CDCl$_3$): 2.64(1H,dd,J=10,14Hz), 3.02(1H,dd,J=5,14Hz), 3.71–3.93(1H,m), 3.86(3H,s), 3.89(6H,s), 3.90(3H,s), 4.24–4.36(2H,m), 5.93(2H,s), 6.28(1H,d,J=1.5Hz), 6.34(1H,d,J=1.5Hz), 6.77(2H,s), 7.52(1H,d,J=2Hz)

IR $\gamma$max (CHCl$_3$) cm$^{-1}$: 2940, 1744, 1642, 1584.

MS: 428 (M$^+$), 165 (base).

HRMS (as C$_{23}$H$_{24}$O$_8$): Calculated: 428.14712; Found: 428.14792.

EXAMPLE 6

Preparation of
(3aR,Sbiar)-3a,4-dihydro-8,9,10,11-tetramethoxy-6,7-methylenedioxydibenzo-[4,5:6,7]cycloocta[1,2-c]furan-1(3H)-one and
(3aR,Sbiar)-3a,4-dihydro-6,9,10,11-tetramethoxy-7,8-methylenedioxydibenzo[4,5:6,7]cycloocta[1,2-c]furan-1(3H)-one Ferric perchlorate hexahydrate (18.5 g, 0.04 mol) and trifluoroacetic acid (6 ml) were added at room temperature to a solution of (R)-(E)-3-[1-(5-methoxy-3,4-methylenedioxyphenyl)methyl]-2-(3,4,5-trimethoxybenzylidene)butanolide (6.19 g, 0.014 mol) in dichloromethane (60 ml), followed by stirring at room temperature for 3.5 hours. The reaction mixture was added with 50 ml of saturated NaHCO$_3$ and insoluble matter was filtered off. The filtrate was extracted with dichloromethane (100 ml×3). The organic layers were combined and then dried over anhydrous magnesium sulfate. The solvent was distilled off under reduced pressure. The brown oil thus obtained (5.8 g) was purified by column chromatography (silica gel: "MERCK #9385", 400 g, eluent: 1:10 mixed solvent of ethyl acetate and hexane), whereby 2.055 g of a colorless solid were obtained from fractions containing (3aR,Sbiar)-3a,4-dihydro-8,9,10,11-tetramethoxy-6,7-methylenedioxydibenzo[ 4,5:6,7]cycloocta[1,2-c]furan-1(3H)-one. The solid was recrystallized from a mixed solvent of ethyl acetate and hexane, whereby 1.69 g of (3aS,Rbiar)-3a,4-dihydro-8,9,10,11-tetramethoxy-6,7-methylenedioxydibenzo[4,5:6,7]cycloocta[1,2-c]furan-1(3H)-one were obtained as colorless plate crystals (yield: 27%). From other fractions containing (3aR,Sbiar)-3a,4-dihydro-6,9,10,11-tetramethoxy-7,8-methylenedioxydibenzo[4,5:6,7]cycloocta[1,2-c]furan1(3H)-one, 0.223 g of a pale yellow solid was obtained. The pale yellow solid was recrystallized from a mixed solvent of ethyl acetate and hexane, whereby 0.18 g of (3aR,Sbiar)-3a,4-dihydro-6,9,10,11-tetramethoxy-7,8-methylenedioxydibenzo[4,5:6,7]cycloocta[1,2-c]furan1(3H)-one was obtained as colorless needle crystals (yield: 2.9%). *(3aR,Sbiar)-3a,4-dihydro-8,9,10,11-tetramethoxy-6,7-methylenedioxydibenzo[4,5:6,7]cycloocta[1,2-c]furan-1(3H)-one Melting point: 221°-221.5° C.
$[\alpha]^{27}{}_D$: +340° (C=1.00, CHCl$_3$)
1HNMR (CDCl$_3$): 2.42(1H,dd,J=1,14Hz), 3.00(1H,dd,J=7,14Hz), 3.60-3.80(1H,m), 3.63(3H,s), 3.81(3H's), 3.89(3H,s), 3.91(3H,s), 4.09(1H,dd,J=9,10Hz), 4.44(1H,t, J=9Hz), 5.96(1H,d,J=1.5Hz), 5.98(1H,d,J=1.5Hz), 6.34(1H, s), 6.58(1H,s), 7.51(1H,s).
IR γmax (KBr) cm$^{-1}$: 2940, 1758, 1674, 1620, 1592.
MS: 426 (M+, base).
Elemental analysis (as C$_{23}$H$_{22}$O$_8$): Calculated: C, 64.78; H, 5.20; Found: C, 64.75; H, 5.13. *(3aR,Sbiar)-3a,4-dihydro-6,9,10,11-tetramethoxy-7,8-methylenedioxydibenzo[4,5:6,7]cycloocta[1,2-c]furan-1(3H)-one Melting point: 179.5°-180° C.
$[\alpha]^{27}{}_D$: +369° (C=0.96, CHCl$_3$)
1HNMR (CDCl$_3$): 2.45(1H,dd,J=1.2,15.4Hz), 3.07(1H,dd,J=6.5,14Hz), 3.40-3.61(1H,m), 3.72(3H,s), 3.89(3H,s), 3.91(3H,s), 3.94(3H,s), 4.12(1H,dd,J=8,10Hz), 4.46(1H,t,J=9Hz), 5.88(1H,d,J=1.5Hz), 5.97(1H,d, 1.5Hz), 6.28(1H,s), 6.61(1H,s), 7.51(1H,d,J=3Hz).

IR γmax (KBr) cm$^{-1}$: 2944, 2908, 1746, 1666, 1642, 1590.
MS: 426 (M+, base).
Elemental analysis (as C$_{23}$H$_{22}$O$_8$): Calculated: C, 64.78; H, 5.20; Found: C, 64.71; H, 5.27.

REFERENTIAL EXAMPLE 8

Synthesis of
(S)-3-[1-(3,4,5-trimethoxyphenyl)methyl]butanolide

Dissolved in 5 ml of dichloromethane were 500 mg (2 mmol) of (S)-3-[1-(5-methoxy-3,4-methylenedioxyphenyl)methyl]butanolide. The solution was added with a solution of boron trichloride in dichloromethane (1.0M, 4 ml, 4 mmol), followed by stirring at 0° C. for 45 minutes. After the solvent was distilled off under reduced pressure, the residue was dissolved in a mixture consisting of 10 ml of methanol and 5 ml of 4N-HCl, followed by stirring at room temperature for 1.5 hours. The reaction mixture was dissolved in 50 ml of ethyl acetate and the resulting solution was washed with water and saturated NaCl. The organic layer was dried over anhydrous magnesium sulfate and the solvent was distilled off under reduced pressure, whereby 371 mg of yellow foam were obtained. The foam thus obtained was dissolved in 5 ml of DMF. The solution was thereafter added with 2.6 g (18.8 mmol) of potassium carbonate and 1.3 ml (20.8 mmol) of iodomethane, followed by stirring at 50° C. for one hour. The reaction mixture was made acidic with 2N-HCl. The resultant mixture was extracted with dichloromethane (10 ml×2). The organic layer was combined and was dried over an anhydrous magnesium sulfate, and the solvent was distilled off under reduced pressure. The oil thus obtained was purified by column chromatography (silica gel: "MERCK #9385", eluent: 1:2 mixed solvent of ethyl acetate and hexane), whereby 261 mg of the title compound were obtained as a colorless solid (yield: 49%).

Melting point: 101.5°-103° C. (Colorless prism crystals recrystallized from ethyl acetate).
$[\alpha]^{25}{}_D$: −8.50° (C=1.13, CHCl$_3$)
1HNMR (CDCl$_3$): 2.31(1H,dd,J=7,17Hz), 2.63(1H,dd,J=8,17Hz), 2.71(2H,d,J=9Hz), 2.79-2.94(1H,m), 3.84(3H,s), 3.85(6H,s), 4.06(1H,dd,J=6,9Hz), 4.36(1H, dd,J=7,9Hz), 6.36(2H,s).
IR γmax (KBr) cm$^{-1}$: 2992, 2972, 2928, 1766, 1592, 1506, 1462, 1424, 1336, 1246, 1232, 1170, 1118.
MS: 266 (M+), 181 (base).
Elemental analysis (as C$_{14}$H$_{18}$O$_5$): Calculated: C, 63.14; H, 6.81; Found: C, 63.02; H, 6.87.

REFERENTIAL EXAMPLE 9

Synthesis of
(S)-(E)-2-(3,4,5-trimethoxybenzylidene)-3-[1-(3,4,5-trimethoxyphenyl)-methyl]butanolide A solution of the compound of Referential Example 8 (500 mg, 1.88 mmol) and 3,4,5-trimethoxybenzaldehyde (400 mg, 2.04 mmol) in toluene (15 ml) was added to a hexane solution (1.0 mol/l, 5.6 ml, 5.6 mmol) of lithium hexamethyldisilazide at room temperature under an argon stream, followed by stirring for 30 minutes. The reaction mixture was thereafter added with a solution of acetic anhydride (0.20 ml, 2.0 mmol) in 1 ml of toluene, followed by stirring at room temperature for 30 minutes. Further, a solution of diazabicyclo-undecene (0.37 ml, 2.5 mmol) in 1 ml of toluene was added to the resulting reaction mixture and was stirred at 60° C. for 1 hour.

The reaction mixture thus obtained was washed successively with 2N-HCl (50 ml), saturated NaHCO$_3$ (50 ml) and saturated NaCl (50 ml), followed by drying over anhydrous magnesium sulfate. The solvent was distilled off under reduced pressure, whereby 1.0 g of yellow oil was obtained. The oil was purified by column chromatography (silica gel; "FUJI-DAVIDSON BW300", 20 g, eluent: 1:1 mixed solvent of ethyl acetate and hexane), whereby 0.45 g of the title compound was obtained as pale yellow oil (54%).

[α]$^{26}$$_D$: +77.0° (C=1.07, CHCl$_3$)

$^1$HNMR (CDCl$_3$): 2.65(1H,dd,J=10,14Hz), 3.11(1H,dd,J=5,14Hz), 3.82(3H,s), 3.83(6H,s), 3.89(6H,s), 3.91(3H,s), 3.82–3.91(1H,m), 4.29–4.31(2H,m), 6.38(2H,s), 6.82(2H,s), 7.53(1H,d,J=2Hz).

IR γmax (CHCl$_3$)cm$^{-1}$: 2940, 1748, 1648, 1588, 1496, 1460, 1416, 1336, 1152, 1128, 998.

MS: 444 (M+), 181 (base)

HRMS (as C$_{24}$H$_{28}$O$_8$, M+): Calculated: 444.17833; Found: 444.17793.

EXAMPLE 7

Synthesis of (3aS,Rbiar)-3a,4-dihydro-6,7,8,9,10,11-hexamethoxydibenzo[4,5:6,7]-cycloocta[1,2-c]furan-1(3H)-one A solution of (S)-(E)-2-(3,4,5-trimethoxybenzylidene)-3-[1-(3,4,5-trimethoxyphenyl)methyl]-butanolide (491 mg, 1.1 mmol) in 5 ml of methylene chloride was added with 0.44 ml of trifluoroacetic acid and further with 1.47 (3.2 mol) g of ferric perchlorate, followed by stirring at room temperature for 2 hours. The reaction mixture was dissolved in 40 ml of ethyl acetate. The resulting solution was washed successively with water (50 ml), 2N-HCl (50 ml×2) and saturated NaCl (50 ml). The organic layer was then dried over anhydrous magnesium sulfate. The solvent was distilled off under reduced pressure, whereby 506 mg of brown oil were obtained. The oil was purified by column chromatography (silica gel: "MERCK #9385", 25 g, eluent: 1:1 mixed solvent of ethyl acetate and hexane), whereby 441 mg of the title compound were obtained as pale yellow oil (yield: 90%).

[α]$^{26}$$_D$: −284° (C=0.895, CHCl$_3$)

$^1$HNMR (CDCl$_3$): 2.46(1H,dd,J=1,14H), 3.07(1H,dd,J=7,14Hz), 3.40–3.60(1H,m), 3.59(3H,s), 3.64(3H,s), 3.88(3H,s), 3.89(3H,s), 3.90(3H,s), 3.91(3H,s), 4.11(1H,dd, J=8,10Hz), 4.47(1H,t,J=8Hz), 6.59(1H,s), 6.41(1H,s), 7.53(1H,d,J=3Hz).

IR γmax (CHCl$_3$)cm$^{-1}$: 2940, 1754, 1668, 1596, 1578, 1484, 1460, 1396, 1346, 1316, 1162, 1128, 1106, 1016, 1002.

MS: 442 (M+, base).

HRMS (as C$_{24}$H$_{26}$O$_8$; M+): Calculated: 442.16279; Found: 442.16279.

REFERENTIAL EXAMPLE 10

Preparation of 1-methyl hydrogen (S)-2-[1-(5-methoxy-3,4-methylenedioxyphenyl)methyl]-butanedioate Dissolved in 640 ml of hot acetone were 20 g of 1-methyl hydrogen (RS)-2-[1-(5-methoxy-3,4-methylenedioxyphenyl)methyl]butanedioate (racemic mixture) and 8.65 g of D-(+)-α-aminocaprolactam, followed by stirring at room temperature for 3 hours. Precipitated crystals were collected by filtration, whereby 17.54 g of the aminocaprolactam salt of the title compound were obtained. The salt was dissolved in 200 ml of saturated NaHCO$_3$. The resulting solution was washed with ether (200 ml×3) and was then acidified with a 10% aqueous oxalic acid solution, followed by extraction with dichloromethane (500 ml×3). The dichloromethane layers were combined, washed with saturated NaCl and then dried over anhydrous magnesium sulfate. The solvent was distilled off under reduced pressure, whereby 12.29 g of 1-methyl hydrogen (RS)-2-[1-(5-methoxy-3,4-methylenedioxyphenyl)methyl]butanedioate of about 60% e.e. were obtained. The compound was stirred in 20 ml of methanol at room temperature for 1 hour. Insoluble matter was removed by filtration. The filtrate was distilled off under reduced pressure, whereby 5.04 g of the title compound of 100% e.e. were obtained.

Melting point: 96.5°–97.0° C. (Colorless prism crystals).

[α]$^{23}$$_D$: −26.6° (C=1.18, CHCl$_3$)

$^1$HNMR (CDCl$_3$): 2.46(1H,dd,J=4.5,17Hz), 2.62–2.77(2H,m), 2.93–3.13(2H,m), 3.69(3H,s), 3.88(3H,s), 5.94(2H,s), 6.31(1H,s), 6.34(1H,s).

Protons of any carboxylic acid were not observed at all.

IR γmax (KBr) cm$^{-1}$: 3136, 2912, 1724, 1680, 1638, 1512.

MS: 296 (M+), 165 (base).

Elemental analysis (as C$_{14}$H$_{16}$O$_7$): Calculated: C, 62.39; H, 5.64; Found: C, 62.38; H, 5.69.

REFERENTIAL EXAMPLE 11

Synthesis of (S)-3-[1-(5-methoxy-3,4-methylenedioxyphenylmethyl]-butanolide

Dissolved in 900 ml of ethanol were 71.8 g (0.24 mol) of 1-methyl hydrogen (S)-2-[1-(5-methoxy-3,4-methylenedioxyphenyl)methyl]butanedioate, followed by the addition of a solution of potassium hydroxide (85%, 16.7 g, 0.27 mol) in 450 ml of ethanol. The resulting solution was added with 51.6 g (0.46 mol) of calcium chloride and 36 g (0.95 mol) of sodium borohydride under ice cooling, followed by stirring at 0° C. for 19 hours. The reaction mixture was added with 500 ml of 12N-HCl under ice cooling, stirred at room temperature for 30 minutes and then extracted with methylene chloride (300 ml×3). The organic layers were combined, washed with saturated NaHCO$_3$ and then with saturated NaCl, followed by drying over anhydrous magnesium sulfate. The solvent was distilled off under reduced pressure, whereby 68.76 g of a colorless solid were obtained. The solid was recrystallized from a mixed solvent of ethyl acetate and hexane, whereby 46.85 g of the title compound were obtained as colorless prism crystals (yield: 75%).

Melting point: 88.5°–89° C.

[α]$^{23}$$_D$: −6.82° (C=1.12, CHCl$_3$).

1HNMR (CDCl$_3$): 2.27(1H,dd,J=7,17Hz), 2.55–2.89(4H,m), 3.90(3H,s), 4.03(1H,dd,J=6,9Hz), 4.34(1H,dd,J=7,9Hz), 5.95(2H,s), 6.30(1H,d,J=2Hz), 6.34(1H,d,J=2Hz).

IR γmax (KBr) cm$^{-1}$: 1784, 1768, 1632, 1510.

MS: 250 (M+), 165 (base)

REFERENTIAL EXAMPLE 12

Synthesis of (S)-(E)-3-[1-(5-methoxy-3,4-methylenedioxyphenyl)methyl]-2-(3,4,5-trimethoxybenzylidene)butanolide A solution of (S)-3-[1-(5-methoxy-3,4-methylenedioxyphenyl)methyl]butanolide (25.0 g, 0.1 mol) and 3,4,5-trimethoxybenzaldehyde (31.0 g, 0.16 mol) in 400 ml of toluene was cooled to 0° C. under an argon stream, followed by the addition of 10.8 g of sodium hydride (60%, 0.27 mol) and 0.4 ml (0.01 mol) of methanol. After stirred at 0° C. for 15 minutes and further at room temperature for 48 hours, the reaction mixture was ice-cooled and added with 100 ml of 6N-HCl. After the removal of the water layer, the organic layer was washed successively with water, saturated $NaHCO_3$ and saturated NaCl, and then dried over anhydrous magnesium sulfate. The residue obtained by distilling off the solvent was purified by column chromatography (silica gel: "MERCK #9385", 500 g, eluent: 1:2 mixed solvent of ethyl acetate and hexane), whereby 20.38 g of the title compound were obtained as colorless oil (yield: 48%).

$[\alpha]^{25}_D$: +55.1 (C=0.955, $CHCl_3$)

$^1$HNMR ($CDCl_3$): 2.64(1H,dd,J=10,14Hz), 3.01(1H,dd,J=5,14Hz), 3.83–3.90(1H,m), 3.86(3H,s), 3.89(6H,s), 3.90(3H,s), 4.22–4.36(2H,m), 5.93(2H,s), 6.28(1H,d,J=1.5Hz), 6.33(1H,d,J=1.5Hz), 6.77(2H,s), 7.51(1H,d,J=1.7Hz).

IR $\gamma$max (KBr) $cm^{-1}$: 1746, 1644, 1582.

MS: 428 (M+), 263 (base).

HRMS (as $C_{23}H_{24}O_8$): Calculated: 428.14707; Found: 428.14677.

REFERENTIAL EXAMPLE 13

Synthesis of (S)-(E)-3-[1-(3,4-dihydroxy-5-methoxyphenyl)methyl]-2-(3,4,5-trimethoxybenzylidene)-butanolide In 10 ml of dichloromethane, 0.84 g (1.96 mmol) of (S)-(E)-3-[1-(5-methoxy-3,4-methylenedioxyphenyl)methyl]-2-(3,4,5-trimethoxybenzylidene)butanolide was dissolved. The solution was added with 4 ml of a 1.0M dichloromethane solution of boron trichloride (4 mmol), followed by stirring at 0° C. for 30 minutes. The solvent was distilled off under reduced pressure. After the residue was dissolved in a mixture consisting of 20 ml of methanol and 6 ml of 2N-HCl, the solution was stirred at 0° C. for 2 hours. The reaction mixture was extracted with ethyl acetate (50 ml×1, 20 ml×2). The organic layers were combined and washed successively with water and saturated $NaHCO_3$, followed by drying over anhydrous magnesium sulfate. The solvent was distilled off under reduced pressure, whereby 0.79 g of the title compound was obtained as pale yellow oil (yield: 97%).

$[\alpha]^{27}_D$: +50.3. (C=0.70, $CHCl_3$)

$^1$HNMR ($CDCl_3$): 2.60(1H,dd,J=10,14Hz), 3.04(1H,dd,J=4,14Hz), 3.78–3.90(1H,m), 3.83(3H,s), 3.89(6H,s), 3.90(3H,s), 4.24–4.37(2H,m), 5.31(1H,s), 5.36(1H,s), 6.23(1H,d,J=2Hz), 6.43(1H,d,J=2Hz), 6.79(2H,s), 7.51(1H,d,J=2Hz).

IR $\gamma$max ($CHCl_3$)$cm^{-1}$: 3556, 2940, 1746, 1646, 1620, 1582.

MS: 416 (M+), 263 (base).

HRMS (as $C_{22}H_{24}O_8$): Calculated: 416.14702; Found: 416.14652.

EXAMPLE 8

Synthesis of (3aS,Rbiar)-3a,4-dihydro-6,7-dihydroxy-8,9,10,11-tetramethoxydibenzo[4,5:6,7]-cycloocta[1,2-c]furan-1(3H)-one Dissolved in 6 ml of dichloromethane were 200 mg (0.48 mmol) of (S)-(E)-3-[1-(3,4-dihydroxy-5-methoxyphenyl)methyl]-2-(3,4,5-trimethoxybenzylidene)-butanolide. The solution was added with 6 ml of trifluoroacetic acid and 500 mg (1.08 mmol) of ferric perchlorate, followed by stirring at room temperature for 1 hour and 15 minutes. The reaction mixture was added with saturated $NaHSO_3$ and further with 20 ml of ethyl acetate. The organic layer was washed with water and then with saturated $NaHCO_3$, and then dried over anhydrous magnesium sulfate. The solvent was thereafter distilled off under reduced pressure. Brown oil (280 mg) thus obtained was purified by column chromatography (silica gel: "FUJI-DAVIDSON BW-300", 20 g, eluent: 1:1 mixed solvent of ethyl acetate and hexane), whereby 133 mg of the title compound were obtained as a colorless solid (yield: 67%).

Melting point: 223°–223.5° C. (colorless needle crystals recrystallized from ethyl acetate-hexane)

$[\alpha]_D^{27}$: −282.8° (C=0.29, $CHCl_3$)

$^1$HNMR ($CDCl_3$): 2.42(1H,dd,J=1,14Hz), 3.01(1H,dd,J=6,14Hz), 3.31(3H,s), 3.40–3.60(1H,m), 3.57(3H,s), 3.91(3H,s), 3.93(3H,s), 4.11(1H,dd,J=9,10Hz), 4.46(1H,t,J=9Hz), 5.37(1H,s), 5.53(1H,s), 6.51(1H,s), 6.62(1H,s), 7.50(1H,d,J=3.7Hz).

IR $\gamma$max (KBr) $cm^{-1}$: 3556, 3472, 3284, 2968, 2940, 1756, 1676, 1594, 1492, 1462, 1348, 1304, 1202, 1076.

MS: 414 (M+, base)

EXAMPLE 9

Synthesis of (3aS,Rbiar)-3a,4-dihydro-8,9,10,11-tetramethoxy-6,7-methylenedioxydibenzo[4,5:6,7]-cycloocta[1,2-c]furan-1(3H)-one and (3aS,Rbiar)-3a,4-dihydro-6,9,10,11-tetramethoxy-7,8-methylenedioxydibenzo[4,5:6,7]cycloocta[1,2-c]furan-1(3H)-one Ferric perchlorate hexahydrate (60.0 g, 0.13 mol) and trifluoroacetic acid (20.0 ml) were added to a solution of (S)-(E)-3-[1-(5-methoxy-3,4-methylenedioxyphenyl)methyl]-2-(3,4,5-trimethoxybenzylidene)butanolide (20.0 g, 0.047 mol) in 200 ml of dichloromethane at room temperature, followed by stirring at room temperature for 3.5 hours. The reaction mixture was washed successively with 6N-HCl, water and saturated $NaHCO_3$. After the organic layer was dried over anhydrous magnesium sulfate, the solvent was distilled off under reduced pressure. Brown oil (19.24 g) thus obtained was purified by column chromatography (silica gel: "MERCK #9385", 1 kg, eluent: 1:10–1:2 gradient system of ethyl acetate and hexane), whereby 4.26 g of a colorless solid were obtained from fractions containing (3aS,Rbiar)-3a,4-dihydro-8,9,10,11- tetramethoxy-6,7-methylenedioxydibenzo[4,5:6,7]cycloocta[1,2-c]furan-1(3H)-one. The solid was recrystallized from a mixed solvent of ethyl acetate and hexane, whereby 3.54 g of (3aS,Rbiar)-3a,4-dihydro-8,9,10,11-tetramethoxy- 6,7-methylenedioxydibenzo[4,5:6,7]cycloocta[1,2-c]furan-1(3H)-one were obtained as colorless plate crystals (yield: 18%). From other fractions containing (3aS,Rbiar)-3a,4-dihydro-6,9,10,11-tetramethoxy-7,8-methylenedioxydibenzo[4,5:6,7]cycloocta[1,2-c]furan-1(3H)-one, 0.75 g of a pale yellow solid was obtained. The pale yellow solid was recrystallized from a mixed solvent of ethyl acetate and hexane, whereby 0.55 g of (3aS,Rbiar)-3a,4-dihydro-6,9,10,11-tetramethoxy-7,8-methylenedioxydiben Melting point: 220.5°–221.5° C.

$[\alpha]^{27}_D$: −329° (C=1.165, $CHCl_3$)

¹HNMR (CDCl₃): 2.43(1H,d,J=14Hz), 2.99(1H,dd,J=6,14Hz), 3.40–3.60(1H,m), 3.63(3H,s), 3.81(3H,s), 3.89(3H,s), 3.91(3H,s), 4.44(1H,t,J=9Hz), 4.09(1H,dd,J=9,10Hz), 5.96(1H,d,J=1.5Hz), 5.98(1H,d,J=1.5Hz), 6.58(1H,s), 6.34(3H,s), 7.51(1H,d,J=3Hz).

IR γmax (KBr) cm⁻¹: 2944, 1758, 1674, 1620, 1594.

MS: 426 (M+, base).

Elemental analysis (as C₂₃H₂₂O₈): Calculated: C, 64.78; H, 5.20; Found: C, 64.60; H, 5.01. *(3aS,Rbiar)-3a,4-dihydro-6,9,10,11-tetramethoxy-7,8methylenedioxydibenzo[4,5:6,7]cycloocta[1,2-c]furan-1(3H)-one:

Melting point: 179.0°–180.0° C.

[α]ᴅ²⁷: −359° (C=1.10, CHCl₃)

¹HNMR (CDCl₃): 2.45(1H,d,J=14Hz), 3.07(1H,dd,J=6,14Hz), 3.45–3.62(1H,m), 3.72(3H,s), 3.89(3H,s), 3.91(3H,s), 3.94(3H,s), 4.12(1H,dd,J=8,10Hz), 4.47(1H,t, J=9Hz), 5.88(1H,d,J=1.5Hz), 5.98(1H,d,J=1.5Hz), 6.28(1H,s), 6.62(1H,s), 7.51(1H,d,J=3Hz).

IR γmax (KBr) cm⁻¹: 2940, 2908, 1746, 1666, 1642, 1590.

MS: 426 (M+, base).

Elemental analysis (as C₂₃H₂₂O₈): Calculated: C, 64.78; H, 5.20; Found: C, 64.49; H, 5.06.

REFERENTIAL EXAMPLE 14

Synthesis of (S)-(E)-3-[1-(3,4-dihexyloxy-5-methoxyphenyl)methyl]-2-(3,4,5-trimethoxybenzylidene)butanolide:

Potassium carbonate (500 mg, 3.6 mmol) and 1-iodohexane (1.0 ml, 6.79 mmol) were added to a solution of (S)-(E)-3-[1-(3,4-dihydroxy-5-methoxyphenyl)-methyl]-2-(3,4,5-trimethoxybenzylidene)butanolide (324 mg, 0.78 mmol) in 10 ml of DMF, followed by stirring at 60° C. for 4.5 hours. The reaction mixture was poured into 50 ml of ethyl acetate and then the resulting solution was washed successively with water, 2N-HCl, water and saturated NaHCO₃. After the organic layer was dried over anhydrous magnesium sulfate, the solvent was distilled off under reduced pressure. Brown oil thus obtained was purified by column chromatography (silica gel: "FUJI-DAVIDSON BW-300", eluent: 1:3 mixed solvent of ethyl acetate and hexane), whereby 310 mg of the title compound were obtained as colorless oil (yield: 68%).

[α]ᴅ²⁷: +71.1° (C=0.495, CHCl₃)

¹HNMR (CDCl₃): 0.84–1.02(6H,m), 1.23–1.50(12H,m), 1.60–1.84(4H,m), 2.60(1H,dd,J=11,14Hz), 3.10(1H,dd, J=4,14Hz), 3.78–4.00(1H,m), 3.80(3H,s), 3.89(6H,s), 3.91(3H,s), 3.92(4H,t,J=7Hz), 4.24–4.29(2H,m), 6.83(2H,s), 6.36(2H,s), 7.52(1H,d,J=1.7Hz).

IR γmax (CHCl₃) cm⁻¹: 2932, 2860, 1748, 1646, 1584, 1504, 1454, 1428, 1336, 1242, 1202, 1128.

MS: 584 (M+), 237 (base)

EXAMPLE 10

Synthesis of (3aS,Rbiar)-3a,4-dihydro-6,7-dihexyloxy-8,9,10,11-tetramethoxydibenzo-[4,5:6,7]cycloocta[1,2-c]furan-1(3H)-one and (3aS,Rbiar)-3a,4-dihydro-7,8-dihexyloxy-6,9,10,11-tetramethoxydibenzo[4,5:6,7]-cycloocta[1,2-c]furan-1(3H)-one Ferric perchlorate hexahydrate (200 mg, 0.43 mmol) and trifluoroacetic acid (0.5 ml) were added to a solution of (S)-(E)-3-[1-(3,4-dihexyloxy-5-methoxyphenyl)-methyl]-2-(3,4,5-trimethoxybenzylidene)-butanolide (92 mg, 0.16 mmol) in 5 ml of dichloromethane, followed by stirring at room temperature for 1.5 hours. The reaction mixture was washed successively with 2N-HCl, water and saturated NaHCO₃. After the organic layer was then dried over anhydrous magnesium sulfate, the solvent was distilled off under reduced pressure. Brown oil thus obtained (100 mg) was purified by TLC (silica gel: "MERCK #5744", eluent: 1:2 mixed solvent of ethyl acetate and hexane), whereby 44 mg of (3aS,-Rbiar)-3a,4-dihydro-6,7-dihexyloxy-8,9,10,11-tetramethoxydibenzo[4,5:6,7]cycloocta[1,2-c]-furan-1(3H)-one were obtained as colorless oil (yield: 48%) and 24 mg of (3aS,Rbiar)-3a,4-dihydro-7,8-dihexyloxy-6,9,10,11-tetramethoxydibenzo[4,5:6,7]cycloocta[1,2-c]furan-1(3H)-one were obtained as colorless oil (yield: 26%), respectively. *(3aS,Rbiar)-3a,4-dihydro-6,7-dihexyloxy-8,9,10,11-tetramethoxydibenzo[4,5:6,7]cycloocta[1,2-c]furan-1(3H)-one:

[α]ᴅᴅ²⁷: −225.2° (C=0.50, CHCl₃)

¹HNMR (CDCl₃): 0.89–0.95(6H,m), 1.22–1.56(12H,m), 1.66–1.90(4H,m), 2.43(1H,d,J=14Hz), 3.05(1H,dd,J=7,14Hz), 3.40–3.60(1H,m), 3.60(3H,s), 3.61(3H,s), 3.89(3H,s), 3.91(3H,s), 3.94–4.03(4H,m), 4.10(1H,dd,J=9,10Hz), 4.46(1Ht,J=9Hz), 6.38(1H,s), 6.58(1H,s), 7.52(1H,d,J=3Hz).

IR γmax (CHCl₃) cm⁻¹: 2932, 2864, 1752, 1674, 1594.

MS: 582 (M+, base). *(3aS,Rbiar)-3a,4-dihydro-7,8-dihexyloxy-6,9,10,11-tetramethoxydibenzo[4,5:6,7]cycloocta[1,2-c]furan-1(3H)-one: [α]ᴅ²⁷: −204° (C=0.345, CHCl₃)

¹HNMR (CDCl₃): 0.82(3H,t,J=7Hz), 0.89(3H,t,J=7Hz), 0.99–1.52(14H,m), 1.65–1.82(2H,m), 2.44(1H,dd,J=1,14Hz), 3.05(1H,dd,J=7,14Hz), 3.40–3.63(1H,m), 3.36(1H,dt,J=10,6Hz), 3.71(3H,s), 3.86(3H,s), 3.89(6H,s), 3.93–4.15(4H,m), 4.46(1Ht,J=9Hz), 6.40(1H,s), 6.56(1H,s), 7.50(1H,d,J=3Hz).

IR γmax (CHCl₃) cm⁻¹: 2932, 2860, 1752, 1674, 1594.

MS: 582 (M+, base).

REFERENTIAL EXAMPLE 15

Synthesis of 3,5-dimethoxy-4-(4-nitrobenzyloxy)-benzaldehyde

A solution of syringaldehyde (10 g, 55 mmol), p-nitrobenzyl bromide (13 g, 60 mmol) and potassium carbonate (9.0 g, 65 mmol) in 40 ml of acetone was heated under reflux for 4 hours. The solvent was distilled off under reduced pressure. The residue was added with water and then with dichloromethane. The organic layer was thereafter dried over anhydrous magnesium sulfate. The residue obtained by distilling off the solvent was added with ether, followed by stirring at room temperature. The insoluble colorless solid was collected by filtration to give 16.7 g of the title compound (yield: 93%).

Melting point: 148°–149° C. (Colorless needle crystals recrystallized from ethyl acetate).

IR γmax (KBr) cm⁻¹: 2948, 2844, 1694, 1594, 1526, 1348, 1332.

¹HNMR (CDCl₃): 3.92(6H,s), 5.22(2H,s), 7.14(2H,s), 7.68(2H,d,J=9Hz), 8.21(2H,d,J=9Hz), 9.88(1H,s).

MS: 317 (M+), 181 (base).

Elemental analysis (as $C_{16}H_{15}NO_6$): Calculated: C, 60.56; H, 4.77; N, 4.41. Found: C, 60.36; H, 4.86; N, 4.57.

Referential Example 16

Synthesis of (S)-(E)-2-[3,5-dimethoxy-4-(4-nitrobenzyloxy)benzylidene]-3-(3,4,5-trimethoxybenzyl)butanolide A solution of diisopropylamine (13 ml, 93 mmol) in 80 ml of THF was added with 56 ml (1.66 mol/l, 93 mmol) of n-butyllithium at −60° C. under an argon stream. The resulting solution was cooled below −70° C. and added with a solution of (S)-3-[1-(3,4,5-trimethoxyphenyl)methyl]butanolide (20 g, 75 mmol) in 200 ml of THF. The reaction mixture was added further with a solution of 3,5-dimethoxy-4-(4-nitrobenzyloxy)-benzaldehyde (30 g, 95 mmol) in 400 ml of THF, followed by stirring for 3 minutes. The reaction mixture was added with saturated $NH_4Cl$ and then heated to room temperature. The reaction mixture was added with ethyl acetate and the water layer was removed. The organic layer was washed successively with 2N-HCl, water, saturated $NaHCO_3$ and saturated NaCl, and then dried over anhydrous magnesium sulfate. The solvent was distilled off, whereby 52.7 g of yellow oil were obtained. The oil thus obtained was dissolved in 200 ml of dichloromethane, followed by the addition of 15 ml (108 mmol) of triethylamine, 500 mg (4 mmol) of dimethylaminopyridine and 10 ml (106 mmol) of acetic anhydride. The resulting solution was stirred at room temperature for 9 hours. The reaction mixture was washed successively with 2N-HCl, water, saturated $NaHCO_3$ and saturated NaCl. The organic layer was then dried over anhydrous magnesium sulfate. The solvent was thereafter distilled off from the reaction mixture, whereby 62.2 g of yellow oil were obtained. The oil thus obtained was dissolved in 200 ml of toluene. The resulting solution was added with 20 ml of diazabicycloundecene, followed by stirring at 80° C. for one hour. The reaction mixture was added with ethyl acetate. The organic layer was washed successively with 2N-HCl, water, saturated $NaHCO_3$ and saturated NaCl, and then dried over anhydrous magnesium sulfate. The solvent was distilled off so that 56 g of brown oil were obtained. The brown oil was purified by column chromatography, whereby 41.16 g of the title compound were obtained as colorless oil (97%).

IR $\gamma$max ($CHCl_3$) cm$^{-1}$: 3012, 2968, 2940, 1748, 1648, 1588, 1522.

$[\alpha]^{26}D$: +49.16. (C=0.895, $CHCl_3$)

$^1$HNMR ($CDCl_3$): 2.66(1H,dd,J=10,14Hz), 3.08(1H,dd,J=5,14Hz), 3.60–3.80(1H,m), 3.81(3H,s), 3.82(6H,s), 3.87(6H,s], 4.29–4.32(2H,m), 5.17(2H,s),6.37(2H,s), 6.81(2H,s), 7.53(1H,d,J=1.5Hz), 7.67(2H,d,J=9Hz), 8.22(2H,d,J=9Hz).

MS: 565 (M+), 181(base).

EXAMPLE 11

Synthesis of (3aS,Rbiar)-3a,4-dihydro-6,7,8,9,11-pentamethoxy-10-(4-nitrobenzyloxy)dibenzo[4,5:6,7]cycloocta[1,2-c]furan-1(3H)-one Dissolved in 500 ml of dichloromethane were 27.0 g (47.8 mmol) of (S)-(E)-2-[3,5-dimethoxy-4-(4-nitrobenzyloxy)benzylidene]-3-(3,4,5-trimethoxybenzyl)-butanolide. The resulting solution was added with 50 ml of trifluoroacetic acid and further with 53.0 g (115 mmol) of ferric perchlorate, followed by stirring at room temperature for 3 hours. The reaction mixture was dissolved in ethyl acetate. The organic layer was washed successively with 2N-HCl, water, saturated $NaHCO_3$ and saturated NaCl. The organic layer was then dried over anhydrous magnesium sulfate. The oil obtained by distilling off the solvent was purified by column chromatography, whereby 25.6 g of the title compound were obtained as a pale yellow solid (yield: 95%).

Melting point: 170.5°–171.5° C. (Colorless prism crystals recrystallized from ethyl acetate).

IR $\gamma$max (KBr) cm$^{-1}$: 2940, 1754, 1672, 1596.

$[\alpha]^{29}D$: −256° (C=1.01, $CHCl_3$)

$^1$HNMR ($CDCl_3$): 2.47(1H,dd,J=1.5,14Hz), 3.02(1H,dd,J=7,14Hz), 3.40–3.64(1H,m), 3.56(3H,s), 3.60(3H,s), 3.88(6H,s), 3.89(3H,s), 4.11(1H,dd,J=8,10Hz), 4.48(1Ht,J=8Hz), 5.20(2H,s), 6.42(1H,s), 6.61(1H,s), 7.52(1H,d, J=3.4Hz), 7.68(2H,d,J=9Hz), 8.23(2H,d,J=9Hz).

MS: 563 (M+), 428 (base).

Elemental analysis (as $C_{30}H_{29}NO_{10}$): Calculated: C, 63.94; H, 5.19; N, 2.49. Found: C, 63.73; H, 5.09; N, 2.57.

REFERENTIAL EXAMPLE 17

Synthesis of (S)-(E)-2-[3,4,5-trimethoxybenzylidene]-3-(3-methoxy-4,5-bis(4-nitrobenzyloxy)benzyl)butanolide A solution of (S)-(E)-3-[1-(3,4-dihydroxy-5-methoxyphenyl)methyl-2-(3,4,5-trimethoxybenzylidene)butanolide) (2 g, 4.8 mmol), para-nitrobenzyl bromide (3.05 g, 14.1 mmol) and potassium carbonate (2.03 g, 14.7 mmol) in 70 ml of acetone was heated under reflux for 2.5 hours. After the solvent was distilled off from the reaction mixture under reduced pressure, the residue was added with water and then with dichloromethane. The organic layer was dried over anhydrous magnesium sulfate. The residue obtained by distilling off the solvent from the organic layer was added with ether, followed by stirring at room temperature. The insoluble material was collected by filtration to give 2.88 g of the title compound (yield: 87%).

Melting point: 171°–172° C. (Colorless needle crystals recrystallized from ethyl acetate).

$[\alpha]^{27}D$: −20.4° (C=0.495, $CHCl_3$)

IR $\gamma$max (KBr) cm$^{-1}$: 2940, 1748, 1646, 1584, 1514, 1346.

$^1$HNMR ($CDCl_3$): 2.74(1H,dd,J=9,14Hz), 3.00(1H,dd,J=5,14Hz), 3.70–3.90(1H,m), 3.82(3H,s), 3.87(6H,s), 3.90(3H,s), 4.20–4.37(2H,m), 5.07(2H,s), 5.11(2H,s), 6.36(1H,d,J=1.7Hz), 6.42(1H,d,J=1.7Hz), 6.78(2H,s), 7.52(1H,d,J=2Hz), 7.53(2H,d,J=9Hz), 7.61(2H,d,J=9Hz), 8.18(2H,d,J=9Hz), 8.22(2H,d,J=9Hz).

MS: 686 (M+), 263(base).

Elemental analysis (as $C_{36}H_{34}N_2O_{12}$): Calculated: C, 62.97; H, 4.99; N, 4.08. Found: C, 62.73; H, 5.01; N, 4.31.

EXAMPLE 12

Synthesis of (3aS,Rbiar)-3a,4-dihydro-8,9,10,11-tetramethoxy-6,7-bis(4-nitrobenzyloxy)dibenzo-[4,5:6,7]cycloocta[1,2-c]furan-1(3H)-one and (3aS,Rbiar)-3a,4-dihydro-6,9,10,11-tetramethoxy-7,8-bis(4-nitrobenzyloxy)dibenzo[4,5:6,7]-cycloocta[1,2-c]furan-1(3H)-one In 60 ml of dichloromethane, 2.50 g (3.64 mmol) of (S)-(E)-2-[3,4,5-trimethoxybenzylidene]-3-(3-methoxy- 4,5-bis(4-nitrobenzyloxy)benzyl)butanolide were dissolved. The resulting solution was added with 6 ml of trifluoroacetic acid and 4 g (8.65 mmol) of ferric perchlorate, followed by stirring at room temperature for 4 hours. After the reaction mixture was dissolved in ethyl acetate, the organic layer was washed successively with 2N-HCl, water, saturated NaHCO$_3$ and saturated NaCl, and then dried over anhydrous magnesium sulfate. The oil obtained by distilling off the solvent from the reaction mixture was purified by column chromatography, whereby 1.45 g in total of (3aS,Rbiar)-3a,4-dihydro-8,9,10,11-tetramethoxy-6,7-bis(4-nitrobenzyloxy)dibenzo[4,5:6,7]cycloocta[1,2-c]furan-1(3H)-one and (3aS,-Rbiar)-3a,4-dihydro-6,9,10,11-tetramethoxy-7,8-bis(4-nitrobenzyloxy)dibenzo[4,5:6,7]-cycloocta[1,2-c]furan-1(3H)-one were obtained as pale yellow oil (yield: 58%).

IR $\gamma$max (CHCl$_3$) cm$^{-1}$: 3000, 2940, 2860, 1754, 1674, 1604, 1348.

$^1$HNMR (CDCl$_3$): 2.42–2.50(1H,m), 3.02–3.08(1H,m), 3.40–3.64(1H,m), 3.57(1H,s), 3.58(2H,s), 3.63(1H,s), 3.83(2H,s), 3.88(2H,s), 3.90(2H,s), 3.91(1H,s), 3.92(1H,s), 4.07(1H,dd,J=8,10Hz), 4.40–4.58(1H,m), 4.64(0.7H,d,J=12Hz), 5.02(0.7H,d,J=12Hz), 5.14–5.30(2.6H,m), 6.46(0.3H,s), 6.49(0.7H,s), 6.54(0.7H,s), 6.61(0.3H,s), 7.06(1.3H,d,J=9Hz), 7.37(0.7H,d,J=2.6Hz), 7.56–7.63(3H,m), 8.02(1.3H,d,J=9Hz), 8.17(1.3H,d,J=9Hz), 8.25(1.4H,d,J=9Hz).

MS: 684 (M+), 548(base).

REFERENTIAL EXAMPLE 18

Synthesis of 3,4-dimethoxy-5-[(2-methoxyethoxy)-methoxy]benzaldehyde (1) In 600 ml of water, 200 g (1.18 mol) of gallic acid were suspended. While vigorously stirred, the suspension was added dropwise with 720 ml of an aqueous solution of 300 g (7.5 mmol) of sodium hydroxide and 480 ml (3.8 mmol) of dimethyl sulfate over 6 hours. After further stirred at room temperature for 13 hours, the reaction mixture was added with 6N-HCl. The reaction mixture was extracted with ethyl acetate (500 ml×3). The organic layers were combined together, washed with water and then dried over anhydrous magnesium sulfate. The residue obtained by distilling off the solvent from the organic layer was dissolved in 1 l of methanol. The resulting solution was added with 20 ml of concentrated sulfuric acid, followed by heating under reflux for 20 hours. After the reaction mixture was allowed to cool down to room temperature, the solvent was distilled off. The residue was thereafter added with 70 g of sodium carbonate and ice, followed by extraction with ethyl acetate (500 ml×1, 300 ml×2). The organic layers were combined together and then extracted with ice-cooled 4N-NaOH (100 ml×4). Just after the separation, the water layer extracted with the NaOH was made acidic with ice-cooled 6N-HCl (400 ml). The acidified water layer was extracted with ethyl acetate (300 ml×2). The organic layers were combined together, washed with saturated NaHCO$_3$ and then dried over anhydrous magnesium sulfate. The solvent was distilled off from the organic layer, whereby 67.7 g of the residue mainly composed of methyl 3,4-dimethoxy-5-hydroxybenzoate were obtained as brown oil (yield: 27%).

$^1$HNMR (CDCl$_3$): 3.90–4.00(9H,m), 5.92(1H,s), 7.20–7.50(2H,m). (2) While stirred in 140 ml of THF solution, 30.5 g (0.14 mol) of the methyl ester obtained above were added with 7.5 g (60% in oil, 0.19 mol) of sodium hydride at 0° C. Five minutes later, the reaction mixture was added further with 20 ml (0.17 mol) of methoxyethoxymethyl chloride, followed by stirring at 0° C. for 10 minutes. After the reaction mixture was heated under reflux for 2 hours, the reaction mixture was added with 3.0 g (60% in oil, 76 mmol) of sodium hydride and 10 ml (85 mmol) of methoxyethoxymethyl chloride, followed by heating under reflux for 5 hours. The reaction mixture was added with saturated NH$_4$Cl and then with 300 ml of ethyl acetate and the water layer was removed. The organic layer was washed successively with 2N-HCl, water and saturated NaHCO$_3$, and then dried over anhydrous magnesium sulfate. The residue obtained by distilling off the solvent was purified by column chromatography, whereby 34.33 g of methyl 3-(2-methoxyethoxy)methoxy-4,5-dimethoxybenzoate were obtained as colorless oil (yield: 80%).

$^1$HNMR (CDCl$_3$): 3.40(3H,s), 3.50–3.70(2H,m), 3.90–4.00(11H,m), 5.40(2H,s), 7.25–7.60(2H,m).

(3) In 50 ml of THF, 3.0 g (80 mmol) of lithium aluminum hydride were suspended. While being cooled at 0° C. in argon, the suspension was added dropwise over 10 minutes with a solution of methyl 3-(2-methoxyethoxy)-methoxy-4,5-dimethoxybenzoate (34 g, 0.11 mol), which had been obtained in above (2), in 50 ml of THF. After stirred at 0° C. for 4 hours, the reaction mixture was added with sodium sulfate decahydrate to terminate the reaction. Insoluble matter was removed by filtration. The solvent was distilled off from the filtrate, whereby 30.45 g of the benzyl alcohol derivative were obtained as colorless oil (yield: 99%).

Dissolved in 300 ml of toluene were 30 g of the benzyl alcohol derivative. The resulting solution was added with 100 g (1.1 mol) of activated manganese dioxide, followed by stirring at room temperature for 22 hours. Insoluble matter was removed by filtration and the filtrate was thereafter concentrated, whereby 27.9 g of the title compound were obtained as colorless oil (yield: 94%).

IR $\gamma$max (neat) cm$^{-1}$: 2984, 1694, 1588.

$^1$HNMR (CDCl$_3$): 3.40(3H,s), 3.50–3.68(2H,m), 3.88–4.00(8H,m), 5.40(2H,s), 7.16–7.30(2H,m), 9.92(1H,s).

MS: 270 (M+), 59 (base).

REFERENTIAL EXAMPLE 19

Synthesis of (S)-(E)-2-(3,4-dimethoxy-5-hydroxybenzylidene)-3-(3,4,5-trimethoxybenzyl)butanolide n-Butyllithium (28 ml, 1.66 mol/l, 47 mmol) were added at −60° C. to a solution of diisopropylamine (6.6 ml, 47 mmol) in 50 ml of THF under an argon gas stream, followed by cooling below −70° C. The reaction mixture was added with a solution of (S)-3-[1-(3,4,5-trimethoxyphenyl)methyl]butanolide (10 g, 37.6 mmol) in 60 ml of THF, followed by stirring for 30 minutes. The reaction mixture was added further with a solution of 3,4-dimethoxy-5-[(2-methoxyethoxy)methoxy]benzaldehyde (11.2 g, 41.5 mmol) in 20 ml of THF, followed by stirring for 3 minutes. The reaction mixture was added with saturated NH$_4$Cl, and then heated to room temperature. The reaction mixture was added with ethyl acetate and the water layer was then removed. The organic layer was washed successively with 2N-HCl, water, saturated NaHCO₃ and saturated NaCl and then, dried over anhydrous magnesium sulfate. The solvent was thereafter distilled off, whereby 19 g of yellow oil were obtained. The residue thus obtained was dissolved in 100 ml of dichloromethane and then added with 8 ml (57.8 mmol) of triethylamine, 200 mg (1.6 mmol) of dimethylaminopyridine and 5 ml (53 mmol) of acetic anhydride, followed by stirring at room temperature for 30 minutes. The reaction mixture was washed successively with 2N-HCl, water, saturated NaHCO₃ and saturated NaCl, and then dried over anhydrous magnesium sulfate. The solvent was thereafter distilled off, whereby yellow oil was obtained. The yellow oil thus obtained was dissolved in 60 ml of toluene and added with 10 ml of diazabicycloundecene, followed by stirring at 70° C. for one hour. The reaction mixture was added with ethyl acetate. The organic layer was washed successively with 2N-HCl, water, saturated NaHCO₃ and saturated NaCl, and then dried over anhydrous magnesium sulfate. The solvent was distilled off, whereby 18.75 g of brown oil were obtained. The brown oil was dissolved in 190 ml of dichloromethane and added with a solution of boron trichloride (1.0M, 50 mmol) in 50 ml of dichloromethane, followed by stirring at 0° C. for 10 minutes. The reaction mixture was added with saturated NaHCO₃. The organic layer was separated and then dried over anhydrous magnesium sulfate. The residue obtained by distilling off the solvent from the organic layer was purified by column chromatoqraphy, whereby 10.1 g of the title compound were obtained as colorless oil (62.5 %).

IR γmax (CHCl₃) cm⁻¹: 3532, 3008, 2940, 1746, 1648, 1590.

¹HNMR (CDCl₃): 2.58(1H,dd,J=12,15Hz), 3.04(1H,dd,J=6,15Hz), 3.70-3.90(1H,m), 3.86(3H,s), 3.93(6H,s), 3.94(3H,s), 4.00(3H,s), 4.22-4.40(2H,m), 5.93(1Hbr), 6.50(2H,s), 6.66(1H,d,J=2Hz), 7.03(1H,d,J=2Hz), 7.52(1H,d,J=2Hz).

MS: 430 (M+), 181 (base).

REFERENTIAL EXAMPLE 20

Synthesis of (S)-(E)-2-[3,4-dimethoxy-5-(4-nitrobenzyloxy)benzylidene]-3-(3,4,5-trimethoxybenzyl)butanolide:

A solution of (S)-(E)-2-(3,4-dimethoxy-5-hydroxybenzylidene)-3-(3,4,5-trimethoxybenzyl)butanolide (7.5 g, 17.4 mmol), p-nitrobenzyl bromide (4.6 g, 21.3 mmol) and potassium carbonate (3.0 g, 21.7 mmol) in 100 ml of acetone was heated under reflux for 3.5 hours. After the solvent was distilled off under reduced pressure, the residue was added with water and then ethyl acetate. The organic layer was washed successively with 2N-HCl, water, saturated NaHCO₃ and saturated NaCl and then, dried over anhydrous magnesium sulfate. The solvent was thereafter distilled off. The residue thus obtained was purified by column chromatography, whereby 9 g of the title compound were obtained as colorless foam (yield: 91%).

$[\alpha]^{24}_D$: 45.6° (C=0.645, CHCl₃)

IR γmax (CHCl₃) cm⁻¹: 3012, 2968, 1746, 1648, 1590, 1524, 1348.

¹HNMR (CDCl₃): 2 58-2.73(1H,m), 3.01(1H,dd,J=4,14Hz), 3.75-3.90(1H,m), 3.80(6H,s), 3.81(3H,s), 3.90(3H,s), 3.93(3H,s), 4.25-4.40(2H,m), 5.20(2H,s), 6.36(2H,s), 6.77(1H,d,J=1.7Hz), 6.86(1H,d,J=1.7Hz), 7.48(1H,d,J=1.7Hz), 7.59(2H,d,J=9Hz), 8.23(2H,d,J=9Hz).

MS: 565 (M+), 181 (base).

EXAMPLE 13

Synthesis of (3aS,Rbiar)-3a,4-dihydro-6,7,8,10,11-pentamethoxy-9-(4-nitrobenzyloxy)-dibenzo[4,5:6,7]cycloocta[1,2-c]furan-1(3H)-one and (3aS,Rbiar)-3a,4-dihydro-6,7,8,9,10-pentamethoxy-11-(4-nitrobenzyloxy)dibenzo[4,5:6,7]-cycloocta[1,2-c]furan-1(3H)-one Dissolved in 2 ml of dichloromethane were 91 mg (0.16 mmol) of (S)-(E)-2-[3,4,-dimethoxy-5-(4-nitrobenzyloxy)benzylidene]-3-(3,4,5-trimethoxybenzyl)butanolide. The resulting solution was added with 0.2 ml of trifluoroacetic acid and further with 190 mg (0.41 mmol) of ferric perchlorate, followed by stirring at room temperature for 1.25 hours. The reaction mixture was dissolved in ethyl acetate. The organic layer was washed successively with 2N-HCl, water, saturated NaHCO₃ and saturated NaCl, and then dried over anhydrous magnesium sulfate. The oil obtained by distilling off the solvent was purified by preparative TLC, whereby 77 mq in total of (3aS,Rbiar)-3a,4-dihydro-6,7,8,10,11-pentamethoxy-9-(4-nitrobenzyloxy)dibenzo[4,5:6,7]cycloocta[1,2-c]furan-1(3H)-one and (3aS,Rbiar)-3a,4-dihydro-6,7,8,9,10-pentamethoxy-11-(4-nitrobenzyloxy)dibenzo[4,5:6,7]cycloocta[1,2-c]furan-1(3H)-one were obtained as colorless foam (yield: 85%).

Ir γmax (CHCl₃) cm⁻¹: 3012, 2968, 1754, 1676, 1594, 1522, 1348.

¹HNMR (CDCl₃): 2.27(0.7H,d,J=14Hz), 2.46(0.3H,d,J=14Hz), 3.85(0.7H,dd,J=7,14Hz), 3.09(0.3H,dd,J=7,14Hz), 3.40-3.60(1H,m), 3.58(2H,s), 3.60(1H,s), 3.66(1H,s), 3.79(2H,s), 3.88(1H,s), 3.89(1H,s), 3.90(2H,s), 3.92(4H,s), 3.95(1H,s), 4.08(1Hq, J=9Hz), 4.41-4.49(1H,m), 4.86(0.7H,d,J=13Hz), 5.09(0.7H,d,J=13Hz), 5.24(0.6H,s), 6.33(0.7H,s), 6.49(0.3H,s), 6.61(0.3H,s), 6.64(0.7H,s), 7.13(1.4H,d,J=9Hz), 7.48(0.3H,d,J=3Hz), 7.52(0.7H,d,J=4Hz), 7.67(0.6H,d,J=9Hz), 8.03(1.4H,d,J=9Hz), 8.29(0.6H,d,J=9Hz).

MS: 563 (M+, base).

EXAMPLE 14

Synthesis of methyl 1,2,3-trimethoxy-5H-benzo[3,4]cyclohepta[1,2-f][1,3]benzodioxole-6-carboxylate Ferric perchlorate hexahydrate (342 mg, 0.74 mmol) and 0.5 ml of trifluoroacetic acid were added to a solution of methyl (E)-α-(1,3-benzodioxol-5-yl-methylene)-3,4,5-trimethoxybenzene- propionate [114 mg, 0.295 mmol; P. Magnus et.al., J. Am. Chem. Soc., 107, 4984, (1985)] in 5 ml of dichloromethane, followed by stirring at room temperature for 1 hour. The reaction mixture was dissolved in 20 ml of ethyl acetate. The resulting solution was washed successively with 2N-HCl, water and saturated NaHCO₃, followed by drying over anhydrous magnesium sulfate. The solvent was distilled off under reduced pressure. Brown oil thus obtained (122 mg) was purified by TLC (silica gel: "MERCK #5744", eluent: 1:1 mixed solvent of ethyl acetate and hexane), whereby 96 mg of the title compound were obtained as colorless oil (yield: 85%).

¹H-NMR(CDCl₃): 2.66(1H,dd,J=2,13Hz), 3.49(3H,s), 3.81(3H,s), 3.81(1H,dd,J=2,13Hz), 3.88(3H,s), 3.90(3H,s), 6.02(1H,d,J=1Hz), 6.08(1H,d,J=1Hz), 6.65(1H,s), 6.86(1H,s), 7.33(1H,s), 7.49(1H,s).

Ir γmax (neat) cm$^{-1}$: 2940, 2904, 1702, 1626, 1598, 1482, 1408, 1138, 1104.

MS: 384 (M+), 43 (base).

EXAMPLE 15

Synthesis of 1,5,15,15a-tetrahydro-7,8,9-trimethoxy-3H-[1,3]benzodioxole[5,6-e]-oxazole[3,4-b][2]benzazocin-3-one Dissolved in 1 ml of dichloromethane were 80 mg of 4-[1-(3,4-methylenedioxyphenyl)methyl]-3-[1-(3,4,5-trimethoxyphenyl)methyl] oxazolidin-2-one [0.20 mmol; K. Tomioka, Y. Kubota, H. Kawasaki and K. Koga, Tetrahedron Lett., 30, 2949, (1989)], followed by the addition of 0.2 ml of trifluoroacetic acid and 210 mg (0.45 mmol) of ferric perchlorate. The resulting solution was stirred at room temperature for 40 minutes. The reaction mixture was added with saturated Na$_2$SO$_3$ and was then dissolved in 20 ml of ethyl acetate. The organic layer was washed with water and then with saturated NaHCO$_3$, followed by drying over anhydrous magnesium sulfate. The solvent was distilled off under reduced pressure, whereby brown oil was obtained. The oil was purified by TLC (silica gel: "MERCK #5744", eluent: ether), whereby 71 mg of the title compound were obtained as a colorless solid (yield: 89%).

$^1$HNMR (CDCl$_3$): 2.40–2.68(2H,m), 3.35(1H,d,J=14Hz), 3.62(3H,s), 3.76–3.90(2H,m), 3.90(3H,s), 3.91(3H,s), 4.47–4.67(2H,m), 6.00(1H,d,J=1.5Hz), 6.03(1H,d,J=1.5Hz), 6.71(1H,s), 6.76(1H,s), 6.98(1H,s).

IR γmax (CHCl$_3$) cm$^{-1}$: 2980, 1760, 1620, 1500, 1350, 1160, 1130.

MS: 399 (M+, base)

EXAMPLE 16

Synthesis of (3aRS,13aRS,RSbiar)-3a,4,13,13a-tetrahydro-9,10,11-trimethoxy-6,7-methylenedioxydibenzo[4,5:6,7]cycloocta[1,2-c]furan-1(3H)-one Dissolved in 3 ml of dichloromethane were 88.5 mg of (2RS,3RS)-3-[1-(3,4-methylenedioxyphenyl)-methyl]-2-[1-(3,4,5-trimethoxyphenyl)methyl]butanolide [0.22 mmol, R. D. Damon, R. H. Schlessinger, and J. F. Bount, J. Org. Chem., 41, 3773, (1976)], followed by the addition of 0.4 ml of trifluoroacetic acid and 450 mg (0.98 mmol) of ferric perchlorate. The solution was stirred at room temperature for 3 hours. The reaction mixture was added with saturated Na$_2$SO$_3$ and was dissolved in 20 ml of ethyl acetate. The organic layer was washed with water and then with saturated NaHCO$_3$, and then dried over anhydrous magnesium sulfate. The solvent was distilled off under reduced pressure, whereby brown oil was obtained. The oil was purified by TLC (silica gel: "MERCK #5744", eluent: 1:2 mixed solvent of ethyl acetate and hexane), whereby 65 mg of the title compound were obtained as colorless oil (yield: 74%).

$^1$HNMR (CDCl$_3$): 2.10–2.45(4H,m), 2.64(1H,d,J=13Hz), 3.12(1H,d,J=13Hz), 3.57(3H,s), 3.77(1H,dd,J=8,11Hz), 3.89(3H,s), 3.90(3H,s), 4.37(1H,dd,J=6,8Hz), 5.98(1H,d,J=1.5Hz), 6.00(1H,d,J=1.5Hz), 6.62(1H,s), 6.63(1H,s), 6.70(1H,s).

IR γmax (KBr) cm$^{-1}$: 2944, 2928, 1778, 1596, 1484.

MS: 398 (M+, base)

REFERENTIAL EXAMPLE 21

Synthesis of dimethyl 1,3-bis(3,4,5-trimethoxyphenyl)propane-2,2-dicarboxylate

Under ice cooling, 230 mg of sodium (10 mmol) were dissolved in 15 ml of methanol, followed by the addition of 1.0 ml (8.8 mmol) of dimethyl malonate at room temperature. The solution was added further with 2.3 g of 3,4,5-trimethoxybenzyl bromide (8.8 mmol) and heated under reflux for one hour. After allowed to cool down to room temperature, the reaction mixture was dissolved in 50 ml of ethyl acetate. The resulting solution was washed successively with 2N-HCl, water and saturated NaHCO$_3$. The organic layer was then dried over anhydrous magnesium sulfate. The solvent was distilled off under reduced pressure, whereby 2.6 g of colorless oil were obtained. A solution of the crude oil in 10 ml of methanol was added to a solution of sodium methoxide in methanol, which had been prepared from 200 mg of sodium and 15 ml of methanol, followed by the further addition of 2.3 g (8.8 mmol) of 3,4,5-trimethoxybenzyl bromide. The solution was heated under reflux for one hour. After the reaction mixture was dissolved in 50 ml of ethyl acetate, the resulting mixture was washed successively with 2N-HCl, water and saturated NaHCO$_3$. The organic layer was dried over anhydrous magnesium sulfate and the solvent was distilled off under reduced pressure. The colorless solid thus obtained was recrystallized from a mixed solvent of ethyl acetate and hexane, whereby 1.92 g of the title compound were obtained as colorless prism crystals (yield: 44%).

Melting point: 142.5°–143.0° C. $^1$HNMR (CDCl$_3$): 3.20(4H,s), 3.69(6H,s), 3.81(12H,s), 3.82(6H,s), 6.35(4H,s).

IR γmax (KBr) cm$^{-1}$: 2952, 1730, 1590, 1462, 1424, 1204.

MS: 492 (M+), 181 (base).

EXAMPLE 17

Synthesis of dimethyl 6,7-dihydro-1,2,3,9,10,11-hexamethoxy-5H-dibenzo[a,c]cycloheptene-6,6-dicarboxylate Dissolved in 4 ml of dichloromethane were 200 mg (0.41 mmol) of dimethyl 1,3-bis(3,4,5-trimethoxyphenyl)propane-2,2-dicarboxylate. The solution was added with 0.4 ml of trifluoroacetic acid and 580 mg (1.25 mmol) of ferric perchlorate, followed by stirring at room temperature for 2 hours. After the reaction mixture was added with 2N-HCl and then dissolved in 20 ml of ethyl acetate, the water layer was removed. The organic layer was washed with water and then with saturated NaHCO$_3$, and then was dried over anhydrous magnesium sulfate. The solvent was thereafter distilled off under reduced pressure. The residue thus obtained was purified by column chromatography (silica gel: "MERCK #9385", 10 g, eluent: 1:1 mixed solvent of ethyl acetate and hexane), whereby 183 mg of the title compound were obtained as a colorless solid (yield: 92%).

Melting point: 161°–162° C. (colorless prism crystals recrystallized from a mixed solvent of ethyl acetate and hexane).

$^1$HNMR (CDCl$_3$): 2.73(2H,d,J=14Hz), 3.14(2H,d,J=14Hz), 3.66(6H,s), 3.75(6H,s), 3.87(6H,s), 3.89 (6H,s), 6.59(2H,s).

IR γmax (KBr) cm$^{-1}$: 2956, 1742, 1598, 1576.
MS: 490(M+, base).

REFERENTIAL EXAMPLE 22

Synthesis of (E)-methyl 3-(3,4,5-trimethoxyphenyl)prop-2-enoate

Added to a solution of 8.68 g (0.044 mol) of 3,4,5-trimethoxybenzaldehyde in 50 ml of methanol were 15.0 g (0.044 mol) of methyl (triphenylphosphoranylidene)acetate, followed by stirring at room temperature for 18 hours. The solvent was distilled off under reduced pressure. The residue thus obtained was purified by column chromatography (silica gel: "MERCK #9385", eluent: 1:1 mixed solvent of ethyl acetate and hexane), whereby 11.24 g of the title compound were obtained as a colorless solid (quantitative yield).

$^1$HNMR (CDCl$_3$): 3.81(3H,s), 3.88(3H,s), 3.89(6H,s), 6.35(1H,d,J=16Hz), 6.75(2H,s), 7.61(1H,d,J=16Hz).

IR γmax (KBr) cm$^{-1}$: 3004, 2944, 2840, 1694, 1632, 1584, 1434, 1422, 1338, 1320, 1286, 1248, 1244, 1154, 1122.

MS: 252 (M+, base)

REFERENTIAL EXAMPLE 23

Synthesis of methyl 3-(3,4,5-trimethoxyphenyl)-propanoate

Dissolved in 50 ml of ethyl acetate were 10.2 g of (E)-methyl 3-(3,4,5-trimethoxyphenyl)prop-2-enoate, followed by the addition of 300 mg of 10% palladium carbon. The resulting solution was stirred at room temperature for 19 hours under a hydrogen atmosphere of 1 atm. Insoluble matter was removed by filtration. The filtrate was distilled off under reduced pressure, whereby 11.03 g of the title compound were obtained as colorless oil (quantitative yield).

$^1$HNMR (CDCl$_3$): 2.63(2H,t,J=8Hz), 2.90(2H,t,J=8Hz), 3.69(3H,s), 3.82(3H,s), 3.85(6H,s), 6.42(2H,s).

IR (neat) cm$^{-1}$: 2944, 2840, 1738, 1590, 1508, 1462, 1422, 1242, 1128.

MS: 254 (M+), 44 (base).

REFERENTIAL EXAMPLE 24

Synthesis of 3-(3,4,5-trimethoxyphenyl)propan-1-ol

A solution of methyl 3-(3,4,5-trimethoxyphenyl)-propanoate (11.03 g, 0.043 mol) in tetrahydrofuran (20 ml) was added dropwise to a suspension of lithium aluminum hydride (1.6 g, 0.042 mol) in 20 ml of tetrahydrofuran, said suspension having been cooled to 0° C., followed by stirring at room temperature for 19 hours. After the addition of sodium sulfate decahydrate, the resulting mixture was stirred further at room temperature for one hour. Insoluble matter was removed by filtration and the filtrate was concentrated, whereby 9.5 g of the title compound were obtained as colorless oil (yield: 96.8%).

$^1$HNMR (CDCl$_3$): 1.51(1H,br), 1.85-1.96(2H,m), 2.66(2H,t,J=7Hz), 3.70(2H,t,J=7Hz), 3.82(3H,s), 3.85(6H,s), 6.42(2H,s).

MS: 226 (M+), 181 (base).

REFERENTIAL EXAMPLE 25

Synthesis of 5-(3-bromopropyl)-1,2,3-trimethoxybenzene

To a solution of 3-(3,4,5-trimethoxyphenyl)-propan-1-ol (9.50 g, 0.042 mol) in 50 ml of tetrahydrofuran, 5.0 ml (0.053 mol) of phosphorus tribromide were added dropwise at 0° C., followed by stirring at room temperature for 12 hours. The reaction mixture was added with water under ice cooling. The resulting solution was dissolved in 200 ml of ethyl acetate. The organic layer was washed successively with water, saturated NaHCO$_3$ and saturated NaCl and then dried over anhydrous magnesium sulfate. The solvent was thereafter distilled off under reduced pressure. The oil thus obtained was purified by column chromatography (silica gel: "MERCK #9385", eluent: ether), whereby 10.2 g of the title compound were obtained as colorless oil (yield: 84%).

$^1$HNMR (CDCl$_3$): 2 10-2.23(2H,m), 2.73(2H,t,J=8Hz), 3.37-3.50(2H,m), 3.85(3H,s), 3.88(6H,s), 6.44(2H,s).

IR γmax (neat) cm$^{-1}$: 2996, 2840, 2836, 1590, 1506, 1464, 1454, 1422, 1262, 1246, 1134, 1126, 1008.

MS: 290, 288 (M+), 181 (base).

REFERENTIAL EXAMPLE 26

Synthesis of triphenyl[3-(3,4,5-trimethoxyphenyl)propyl]phosphonium bromide

Dissolved in 50 ml of toluene were 7.65 g (26.5 mmol) of 5-(3-bromopropyl)-1,2,3-trimethoxybenzene and 6.9 g (26.5 mmol) of triphenylphosphine, followed by heating under reflux for 23 hours. The reaction mixture was allowed to cool down to room temperature. The supernatant was thereafter removed by decantation, whereby 7.46 g of crude triphenyl[3-(3,4,5-trimethoxyphenyl)-propyl]phosphonium bromide were obtained as colorless oil (yield: 51%). The crude oil was used in the next reaction without purification.

REFERENTIAL EXAMPLE 27

Synthesis of 1,4-bis(3,4,5-trimethoxyphenyl)-butane

Suspended in 15 ml of THF was 1.0 g of triphenyl[3-(3,4,5-trimethoxyphenyl)propyl]phosphonium bromide (1.8 mmol). The suspension was added with 0.9 ml (1.57M, 1.4 mmol) of butyl lithium in hexane under ice cooling, followed by stirring for one hour. Further, the reaction mixture was added with 280 mg (1.4 mmol) of 3,4,5-trimethoxybenzaldehyde, followed by stirring at room temperature for 21 hours. The reaction mixture was dissolved in 30 ml of ethyl acetate. The resulting solution was washed with water and then with saturated NaCl. After the organic layer was dried over anhydrous magnesium sulfate, the solvent was distilled off under reduced pressure. The oil thus obtained (1.05 g) was purified by column chromatography (silica gel: "MERCK #9385", 50 g, eluent: 1:2 mixed solvent of ethyl acetate and hexane), whereby 438 mg of colorless oil were obtained. The oil was immediately dissolved in a mixture consisting of 7 ml of ethyl acetate and 5 ml of methanol, followed by the addition of 30 mg of a 10% palladium-carbon catalyst. The resulting suspension was stirred at room temperature for 41 hours under a hydrogen atmosphere of I atm. Insoluble matter was removed by filtration and the filtrate was concentrated. The concentrate was thereafter recrystallized from ethyl acetate, whereby 253 mg of the title compound were obtained as colorless prism crystals (yield: 45%).

Melting point: 103°-105° C.

$^1$HNMR (CDCl$_3$): 1.67-1.74(4H,m), 2.52-2.66(4H,m), 3.82(6H,s), 3.84(12H,s), 6.38(4H,s).

IR γmax (KBr) cm$^{-1}$: 2936, 2828, 1590, 1510, 1460, 1422, 1332, 1242, 1122.

MS: 390 (M+, base)

REFERENTIAL EXAMPLE 28

Synthesis of
1-(3,4-dimethoxyphenyl)-4-(3,4,5-trimethoxyphenyl)butane

Suspended in 15 ml of THF were 1.23 g (2.2 mmol) of triphenyl[3-(3,4,5-trimethoxyphenyl)propyl]phosphonium bromide. The suspension was added with 1.4 ml (1.57M, 2.2 mmol) of butyl lithium in hexane under ice cooling, followed by stirring for one hour. The reaction mixture was further added with 365 mg (2.2 mmol) of 3,4-dimethoxybenzaldehyde, followed by stirring at room temperature for 21 hours. After the reaction mixture was dissolved in 30 ml of ethyl acetate, the resulting solution was washed with water and then with saturated NaCl. The organic layer was then dried over anhydrous magnesium sulfate. The solvent was distilled off under reduced pressure. The oil thus obtained (1.31 g) was purified by column chromatography (silica gel: "MERCK #9385", 30 g, eluent: 1:4 mixed solvent of ethyl acetate and hexane), whereby 403 mg of the title compound were obtained as colorless oil. The oil was immediately dissolved in 10 ml of ethyl acetate, followed by the addition of 10 mg of a 10% palladium-carbon catalyst. The resulting suspension was stirred at room temperature for 35 hours under a hydrogen atmosphere of 1 atm. Insoluble matter was removed by filtration and the filtrate was concentrated. The concentrate was purified by column chromatography (silica gel: "MERCK #9385", 10 g, eluent: 1:4 mixed solvent of ethyl acetate and hexane), whereby 198 mq of the title compound were obtained as a colorless solid (25%)

$^1$HNMR (CDCl$_3$): 1.62–1.69(4H,m), 2.51–2.65(4H,m), 3.82(3H,s), 3.84(3H,s), 3.846(3H,s), 3.853(3H,s), 3.86(3H,s), 6.38(2H,s), 6.67–6.81(3H,m).

IR γmax (KBr) cm$^{-1}$: 2996, 2928, 2852, 1588, 1512, 1462, 1454, 1420, 1264, 1238, 1132.

MS: 360 (M+), 181 (base)

REFERENTIAL EXAMPLE 29

Synthesis of
1-(3,4-methylenedioxyphenyl)-4-(3,4,5-trimethoxyphenyl)butane-1-ol

Magnesium (50 mg) was suspended in 0.1 ml of THF at room temperature, to which one drop of ethylene dibromide was added. When the reaction started, the suspension was added with 0.9 ml of THF, followed by the dropwise addition of a solution of 318 mg (1.04 mmol) of 5-(3-bromopropyl)-1,2,3-trimethoxybenzene in THF (1 ml) over 10 minutes. After stirred at room temperature for 4 hours, the reaction mixture was added with a solution of 170 mg (1.13 mmol) of piperonal in 1 ml of THF. The resulting solution was stirred at room temperature for 16 hours, followed by the addition of saturated NH$_4$Cl and further 30 ml of ethyl acetate. The organic layer was washed successively with water and saturated NaCl and then dried over anhydrous magnesium sulfate. The solvent was distilled off under reduced pressure, whereby 0.33 g of oil was obtained. The oil was purified by column chromatography (silica gel: "MERCK #7734", 50 g, eluent: 1:3 mixed solvent of ethyl acetate and hexane), whereby 86 mg of the title compound were obtained as colorless oil (yield: 22%).

$^1$HNMR (CDCl$_3$): 1.59–1.87(5H,m), 2.56(2H,t,J=8Hz), 3.82(3H,s), 3.83(6H,s), 4.61(1Ht,J=7Hz), 5.95(2H,s), 6.36(2H,s), 6.765(1H,s), 6.77(1H,s), 6.85(1H,s).

IR γmax (CHCl$_3$) cm$^{-1}$: 2940, 1592, 1486, 1462, 1128.

MS: 360 (M+), 342 (M+-H$_2$O), 181 (base).

REFERENTIAL EXAMPLE 30

Synthesis of
1-(3,4-methylenedioxyphenyl)-4-(3,4,5-trimethoxyphenyl)butane

Dissolved in 20 ml of ethyl acetate were 500 mg (1.39 mmol) of 1-(3,4-methylenedioxyphenyl)-4-(3,4,5-trimethoxyphenyl)butan-1-ol, followed by the addition of 5 mg of palladium chloride. The resulting mixture was stirred at room temperature for 15 hours under a hydrogen atmosphere of 1 atm. Insoluble matter was removed by filtration and the filtrate was then concentrated. The concentrate thus obtained was purified by column chromatography (silica gel: "MERCK #9385", 50 g, eluent: 1:5 mixed solvent of ethyl acetate and hexane), whereby 388 mg of the title compound were obtained as colorless oil (yield: 81%).

$^1$HNMR (CDCl$_3$): 1.57–1.70(4H,m), 2.46–2.64(4H,m), 3.82(3H,s), 3.84(6H,s), 5.92(2H,s), 6.38(2H,s), 6.61(1H,dd,J=2,8Hz), 6.67(1H,d,J=2Hz), 6.72(1H,d,J=8Hz).

IR γmax (neat) cm$^{-1}$: 2932, 2856, 1590, 1504, 1490, 1462, 1422, 1240, 1128, 1036.

MS: 344 (M+, base)

EXAMPLE 18

Synthesis of
5,6,7,8-tetrahydro-1,2,3,10,11,12-hexamethoxydibenzo[a,c]cyclooctene Dissolved in 1.2 ml (0.128 mmol) of dichloromethane were 50 mg (0.128 mmol) of 1,4-bis(3,4,5-trimethoxyphenyl)butane, followed by the addition of 0.12 ml of trifluoroacetic acid and 178 mg (0.39 mmol) of ferric perchlorate. After stirred at room temperature for 40 minutes, the reaction mixture was dissolved in 20 ml of ethyl acetate. The resulting solution was washed with 2N-HCl and then with saturated NaCl. The organic layer was thereafter dried over anhydrous magnesium sulfate. The solvent was distilled off under reduced pressure, whereby brown oil was obtained. The oil thus obtained was purified by TLC (silica gel: "MERCK #5744", eluent: 1:1 mixed solvent of ethyl acetate and hexane), whereby 3 mg of the title compound were obtained as colorless oil (yield: 6%).

$^1$HNMR (CDCl$_3$): 1.37–1.50(2H,m), 1.96–2.17(4H,m), 2.58(2H,dd, J=8,13Hz), 3.62(6H,s), 3.88(6H,s), 3.90(6H,s), 6.58(2H,s).

IR γmax (CHCl$_3$) cm$^{-1}$: 2932, 2846, 1598, 1460, 1400, 1126, 1104.

MS: 388 (M+, base)

EXAMPLE 19

Synthesis of
5,6,7,8-tetrahydro-1,2,3,10,11-pentamethoxydibenzo[a,c]cyclooctene

In 1 ml of dichloromethane, 70 mg (0.194 mmol) of 1-(3,4-dimethoxyphenyl)-4-(3,4,5-trimethoxyphenyl)-butane were dissolved. The solution was added with 0.1 ml of trifluoroacetic acid and 180 mg (0.39 mmol) of ferric perchlorate, followed by stirring at room temperature for 40 minutes. The reaction mixture was dissolved in 20 ml of ethyl acetate. The resulting solution was washed with 2N-HCl and then with saturated NaCl. The organic layer was dried over anhydrous magnesium sulfate and the solvent was thereafter distilled off under reduced pressure, whereby brown oil was obtained. The oil thus obtained was purified by thin-film chromatography (silica gel: "MERCK #5744", eluent: 1:5 mixed solvent of ethyl acetate and hexane), whereby 17 mg of the title compound were obtained as colorless oil (yield: 24%). In addition, the starting material was recovered as colorless oil (15 mg, recovery: 21%).

$^1$HNMR (CDCl$_3$): 1.44(2H,t,J=10Hz), 1.90–2.20(4H,m), 2.54–2.73(2H,m), 3.54(3H,s), 3.86(3H,s), 3.91(6H,s), 3.93(3H,s), 6.59(1H,s), 6.77(2H,s).

IR $\gamma$max (CHCl$_3$) cm$^{-1}$: 2932, 2856, 1598, 1490, 1462, 1402, 1120, 1078.

MS: 342 (M+, base)

EXAMPLE 20

Synthesis of 5,6,7,8-tetrahydro-1,2,3-trimethoxy-10,11-methylenedioxydibenzo[a,c]cyclooctene In 1 ml of dichloromethane, 73 mg (0.21 mmol) of 1-(3,4-methylenedioxyphenyl)-4-(3,4,5-trimethoxyphenyl)butane were dissolved. The solution was added with 0.1 ml of trifluoroacetic acid and 190 mg (0.41 mmol) of ferric perchlorate, followed by stirring at room temperature for 20 minutes. The reaction mixture was dissolved in 20 ml of ethyl acetate. After the resulting solution was washed with 2N-HCl and then with saturated NaCl, the organic layer was dried over anhydrous magnesium sulfate. The solvent was distilled off under reduced pressure, whereby brown oil was obtained. The oil thus obtained was purified by TLC (silica gel: "MERCK #5744", eluent: 1:5 mixed solvent of ethyl acetate and hexane), whereby 9 mg of the title compound were obtained as colorless oil (yield: 12%). In addition, the starting material were recovered as colorless oil (13 mg, recovery: 18%).

$^1$HNMR (CDCl$_3$): 1.42(2H,t,J=10Hz), 1.90–2.17(4H,m), 2.54–2.63(2H,m), 3.57(3H,s), 3.90(6H,s), 5.96(1H,d,J=1.5Hz), 5.98(1H,d,J=1.5Hz), 6.57(1H,s), 6.71(1H,s), 6.75(1H,s).

IR $\gamma$max (CHCl$_3$) cm$^{-1}$: 2932, 1860, 1596, 1480, 1454, 1406, 1146, 1122, 1104.

MS: 342 (M+, base)

EXAMPLE 21

Synthesis of diethyl 5,6,7,8-tetrahydro-1,2,3-trimethoxy-10,11-methylenedioxydibenzo[a,c]-cyclooctene-6,6-dicarboxylate In 3 ml of dichloromethane, 102 mg of diethyl 4-(3,4-methylenedioxyphenyl)-1-(3,4,5-trimethoxyphenyl)-butane-2,2-dicarboxylate [0.205 mmol, A. S. Kende and L. S. Liebeskind, J. Am. Chem. Soc., 98, 267 (1976)] were dissolved. The solution was added with 0.3 ml of trifluoroacetic acid and 210 mg (0.45 mmol) of ferric perchlorate, followed by stirring at room temperature for 1.5 hours. The reaction mixture was dissolved in 10 ml of ethyl acetate. After the resulting solution was washed with 2N-HCl and then saturated NaCl, the organic layer was dried over anhydrous magnesium sulfate. The solvent was distilled off under reduced pressure, whereby brown oil was obtained. The oil thus obtained was purified by TLC (silica gel: "MERCK #5744", eluent: 1:3 mixed solvent of ethyl acetate and hexane), whereby 62 mg of the title compound were obtained as colorless oil (yield: 61%).

$^1$HNMR (CDCl$_3$): 1.24(3H,t,J=7Hz), 1.26(3H,t,J=7Hz), 2.61–2.75(3H,m), 2.69(1H,d,J=14Hz), 3.25(1H,d,J=14Hz), 3.53(3H,s), 3.83(3H,s), 3.88(3H,s), 4.06(1H,dq,J=11,7Hz), 4.14(1H,dq,J=11,7Hz), 4.19(1H,dq,J=11,7Hz), 4.32(1H,dq,J=11,7Hz), 5.94(1H,d,J=1.5Hz), 5.97(1H,d,J=1.5Hz), 6.59(1H,s), 6.69(1H,s), 6.72(1H,s), 1.52–1.57(1H,m).

IR $\gamma$max (KBr) cm$^{-1}$: 2972, 1936, 1730, 1594, 1484, 1244.

We claim:

1. A process for the preparation of a polycyclic compound represented by the following formula (I):

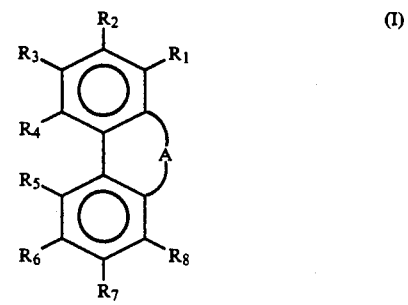

wherein $R_1$–$R_8$ independently represent hydrogen atom, hydroxyl, alkoxyl or substituted or unsubstituted benzyloxy group, or two adjacent $R_1$–$R_8$ substituents are coupled together to form an alkylene dioxy moiety; and A is an alkylene group which is unsubstituted or substituted by one or more alkoxy carbonyl substituents, an alkenylene group which is unsubstituted or substituted by one or more alkoxy carbonyl substituents, or a group represented by any one of the following formulas:

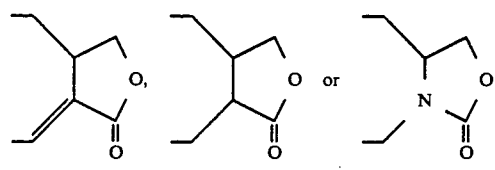

which comprises reacting a compound, represented by the following formula (II):

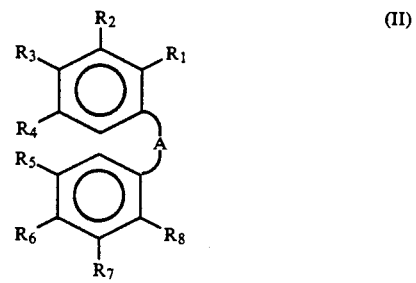

wherein $R_1$–$R_8$ and A have the same meanings as defined above, with ferric perchlorate in the presence of trifluoroacetic acid.

* * * * *